United States Patent
Bhagwat et al.

(10) Patent No.: US 9,499,544 B2
(45) Date of Patent: *Nov. 22, 2016

(54) NITROGEN CONTAINING HETEROCYCLIC COMPOUNDS

(71) Applicant: WOCKHARDT LIMITED, Aurangabad (IN)

(72) Inventors: Sachin Bhagwat, Aurangabad (IN); Prasad Keshav Deshpande, Aurangabad (IN); Satish Bhawsar, Aurangabad (IN); Vijaykumar Jagdishwar Patil, Solapur (IN); Ravikumar Tadiparthi, Aurangabad (IN); Shivaji Sampatrao Pawar, Aurangabad (IN); Sunil Bhaginath Jadhav, Ahmednagar (IN); Sanjay Kisan Dabhade, Pune (IN); Vikas Vitthalrao Deshmukh, Ahmednagar (IN); Bharat Dhond, Aurangabad (IN); Satish Birajdar, Aurangabad (IN); Mohammad Usman Shaikh, Ahmednagar (IN); Deepak Dekhane, Pune (IN); Piyush Ambalal Patel, Anand (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/808,804

(22) Filed: Jul. 24, 2015

(65) Prior Publication Data
US 2015/0336957 A1    Nov. 26, 2015

Related U.S. Application Data

(63) Continuation of application No. 14/298,182, filed on Jun. 6, 2014, now Pat. No. 9,127,004, which is a continuation of application No. 14/113,980, filed as application No. PCT/IB2012/054296 on Aug. 24, 2012, now Pat. No. 9,006,230.

(30) Foreign Application Priority Data

Aug. 30, 2011    (IN) .................. 2424/MUM/2011

(51) Int. Cl.
| | |
|---|---|
| *A61K 31/44* | (2006.01) |
| *A61K 31/43* | (2006.01) |
| *A61K 31/454* | (2006.01) |
| *C07D 471/08* | (2006.01) |
| *A61K 45/06* | (2006.01) |
| *A61K 31/431* | (2006.01) |
| *A61K 31/46* | (2006.01) |
| *A61K 31/424* | (2006.01) |
| *A61K 31/439* | (2006.01) |
| *A61K 31/4545* | (2006.01) |
| *A61K 31/496* | (2006.01) |
| *A61K 31/5377* | (2006.01) |
| *A61K 31/5383* | (2006.01) |
| *A61K 31/546* | (2006.01) |
| *C07D 498/04* | (2006.01) |
| *C07D 519/00* | (2006.01) |

(52) U.S. Cl.
CPC ........... *C07D 471/08* (2013.01); *A61K 31/424* (2013.01); *A61K 31/43* (2013.01); *A61K 31/431* (2013.01); *A61K 31/439* (2013.01); *A61K 31/4545* (2013.01); *A61K 31/46* (2013.01); *A61K 31/496* (2013.01); *A61K 31/5377* (2013.01); *A61K 31/5383* (2013.01); *A61K 31/546* (2013.01); *A61K 45/06* (2013.01); *C07D 498/04* (2013.01); *C07D 519/00* (2013.01)

(58) Field of Classification Search
CPC .............. C07D 451/02; C07D 519/00; A61K 31/551; A61K 2300/00; A61K 31/46
USPC .................... 540/526, 556; 514/211.05, 304
See application file for complete search history.

(56) References Cited

U.S. PATENT DOCUMENTS

2010/0087648 A1    4/2010  Lampilas et al.

FOREIGN PATENT DOCUMENTS

WO    WO/2009/091856    7/2009

*Primary Examiner* — Shengjun Wang
(74) *Attorney, Agent, or Firm* — Bio Intellectual Property Services LLC; O. (Sam) Zaghmout

(57) ABSTRACT

Compounds of Formula (I), their preparation and use in preventing or treating bacterial infections are disclosed.

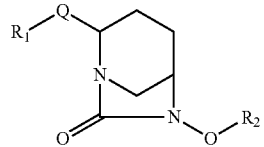

Formula (I)

18 Claims, No Drawings

NITROGEN CONTAINING HETEROCYCLIC COMPOUNDS

This patent application is a continuation of Ser. No. 14/298,182, filed Jun. 6, 2014, which is a continuation of Ser. No. 14/113,980, now U.S. Pat. No. 9,006,230, filed Nov. 30, 2013, which entered the National Phase of Serial No. PCT/IB2012/054296, filed Aug. 24, 2012, which claims the benefit of Indian Provisional Patent Application No. 2424/MUM/2011 filed on Aug. 30, 2011, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to nitrogen containing heterocyclic compounds, their preparation and their use in preventing and/or treating bacterial infections.

BACKGROUND OF THE INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistance. Coates et al. (Br. J. Pharmacol. 2007; 152(8), 1147-1154.) have reviewed novel approaches to developing new antibiotics. However, the development of new antibacterial agents is a challenging task. For example, Gwynn et al. (Annals of the New York Academy of Sciences, 2010, 1213: 5-19) have reviewed the challenges in the discovery of antibacterial agents.

Several antibacterial agents have been described in the prior art (for example, see PCT International Application Nos. PCT/US2010/060923, PCT/EP2010/067647, PCT/US2010/052109, PCT/US2010/048109, PCT/GB2009/050609, PCT/EP2009/056178 and PCT/US2009/041200). However, there remains a need for potent antibacterial agents for preventing and/or treating bacterial infections, including those caused by bacteria that are resistant to known antibacterial agents.

The inventors have surprisingly discovered nitrogen containing heterocyclic compounds with antibacterial properties.

SUMMARY OF THE INVENTION

Accordingly there are provided nitrogen containing heterocyclic compounds, methods for preparation of these compounds, pharmaceutical compositions comprising these compounds, and method for preventing or treating bacterial infection in a subject using these compounds.

In one general aspect, there are provided compounds of Formula (I):

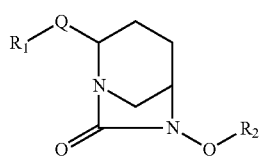

Formula (I)

or a stereoisomer or a pharmaceutically acceptable salt thereof;

wherein:
Q is heteroaryl;
$R_1$ is:
(a) hydrogen,
(b) $(CO)_n$—$R_3$, or
(c) $COOR_4$,
n is 0, 1 or 2;
$R_2$ is:
(a) $SO_3M$,
(b) $SO_2NH_2$,
(c) $PO_3M$,
(d) $CH_2COOM$,
(e) $CF_2COOM$,
(f) CHFCOOM, or
(g) $CF_3$;
M is hydrogen or a cation;
$R_3$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, $NR_5CONR_6R_7$, heterocyclyl, heteroaryl, cycloalkyl or aryl,
(c) CN,
(d) $NR_6R_7$,
(e) $CONR_6R_7$,
(f) $NHCONR_6R_7$,
(g) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(h) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(i) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(j) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(k) cycloalkyl substituted with $C_1$-$C_6$ alkyl wherein $C_1$-$C_6$ alkyl is further substituted with one or more substituents independently selected from $OR_5$, $NR_6R_7$, halogen, CN, or $CONR_6R_7$, or
(l) $OR_8$;
$R_4$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(d) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(e) heteroaryl optionally substituted with one or more substituents independently selected from $C_1$-$C_6$ alkyl, OR$_5$, NR$_6$R$_7$, halogen, CN, CONR$_6$R$_7$, SO$_2$-alkyl, SO$_2$-aryl, OSO$_2$-alkyl, OSO$_2$-aryl, or NHCONR$_6$R$_7$, or
(f) cycloalkyl optionally substituted with one or more substituents independently selected from C$_1$-C$_6$ alkyl, OR$_5$, NR$_6$R$_7$, halogen, CN, CONR$_6$R$_7$, SO$_2$-alkyl, SO$_2$-aryl, OSO$_2$-alkyl, OSO$_2$-aryl, or NHCONR$_6$R$_7$;

R$_5$ and R$_8$ are each independently:
(a) hydrogen, or
(b) C$_1$-C$_6$ alkyl optionally substituted with one or more substituents independently selected from halogen, CN, CONR$_6$R$_7$, NR$_6$R$_7$, heterocyclyl, heteroaryl, cycloalkyl or aryl;

R$_6$ and R$_7$ are each independently:
(a) hydrogen,
(b) C$_1$-C$_6$ alkyl optionally substituted with one or more substituents independently selected from halogen, OR$_5$, CN, COOR$_5$, CONR$_5$R$_8$, NR$_5$R$_8$, NR$_5$COR$_8$, heterocyclyl, heteroaryl, cycloalkyl or aryl,
(c) aryl optionally substituted with one or more substituents independently selected from C$_1$-C$_6$ alkyl, OR$_5$, NR$_5$R$_8$, halogen, CN, CONR$_5$R$_8$, SO$_2$-alkyl, SO$_2$-aryl, OSO$_2$-alkyl, OSO$_2$-aryl, or NHCONR$_5$R$_8$,
(d) heterocyclyl optionally substituted with one or more substituents independently selected from C$_1$-C$_6$ alkyl, OR$_5$, NR$_5$R$_8$, halogen, CN, CONR$_5$R$_8$, SO$_2$-alkyl, SO$_2$-aryl, OSO$_2$-alkyl, OSO$_2$-aryl, or NHCONR$_5$R$_8$,
(e) heteroaryl optionally substituted with one or more substituents independently selected from C$_1$-C$_6$ alkyl, OR$_5$, NR$_5$R$_8$, halogen, CN, CONR$_5$R$_8$, SO$_2$-alkyl, SO$_2$-aryl, OSO$_2$-alkyl, OSO$_2$-aryl, or NHCONR$_5$R$_8$,
(f) cycloalkyl optionally substituted with one or more substituents independently selected from C$_1$-C$_6$ alkyl, OR$_5$, NR$_5$R$_8$, halogen, CN, CONR$_5$R$_8$, SO$_2$-alkyl, SO$_2$-aryl, OSO$_2$-alkyl, OSO$_2$-aryl, or NHCONR$_5$R$_8$, or
(g) R$_6$ and R$_7$ are joined together to form a four to seven member ring.

In another general aspect, there are provided pharmaceutical compositions comprising a compound of Formula (I), or a stereoisomer or a pharmaceutically acceptable salt thereof.

In another general aspect, there is provided a method for preventing or treating bacterial infection in a subject, said method comprising administering to said subject a pharmaceutically effective amount of a compound of Formula (I) or a stereoisomer or a pharmaceutically acceptable salt thereof.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In another general aspect, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In another general aspect, there are provided pharmaceutical compositions comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In another general aspect, there are provided pharmaceutical compositions comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In another general aspect, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered novel nitrogen containing heterocyclic compounds having antibacterial properties.

The term "$C_1$-$C_6$ alkyl" as used herein refers to branched or unbranched acyclic hydrocarbon radical with 1 to 6 carbon atoms. Typical, non-limiting examples of "$C_1$-$C_6$ alkyl" include methyl, ethyl, n-propyl, iso-propyl, n-butyl, iso-butyl, tert-butyl, n-pentyl, iso-pentyl, n-hexyl and the like. The "$C_1$-$C_6$ alkyl" may be unsubstituted, or substituted with one or more substituents. Typical, non-limiting examples of such substituents include halogen, alkoxy, CN, COOH, $CONH_2$, OH, —$NH_2$, —$NHCOCH_3$, cycloalkyl, heterocyclyl, heteroaryl, aryl and the like.

The term "cycloalkyl" as used herein refers to three to seven member cyclic hydrocarbon radicals. The cycloalkyl group optionally incorporates one or more double or triple bonds, or a combination of double bonds and triple bonds, but which is not aromatic. Typical, non-limiting examples of cycloalkyl groups include cyclopropane, cyclobutane, cyclopentane, cyclohexane, and cycloheptane. The cycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, —$OSO_2$-aryl and the like.

The term "heterocyclyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting examples of heterocycloalkyl groups include azetidine, pyrrolidine, 2-oxo-pyrrolidine, imidazolidin-2-one, piperidine, oxazine, thiazine, piperazine, piperazin-2,3-dione, morpholine, thiamorpholine, azapane, and the like. The heterocycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, and the like. The aryl group may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include 1,2,4-oxadiazol, 1,3,4-oxadiazol, 1,3,4-thiadiazol, 1,2,3,4-tetrazol, 1,3-oxazol, 1,3-thiazole, pyridine, pyrimidine, pyrazine, pyridazine, furan, pyrrol, thiophene, imidazole, pyrazole, benzofuran, benzothiophene, benzimidazole, benzoxazole, benzothiazole, thiazole, and the like. The heteroaryl group may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocyclyl, heteroaryl, aryl, $SO_2$-alkyl, $SO_2$-aryl, $OSO_2$-alkyl, $OSO_2$-aryl and the like.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

The term "optionally substituted" as used herein means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference in its entirety, describes various pharmaceutically acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid, or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional groups capable of being converted into salt, each such functional group may be converted to salt independently. For example, in case of compounds containing two basic nitrogen atoms, one basic nitrogen can form salt with one acid while the other basic nitrogen can form salt with another acid. Some compounds according to the invention contain both, acidic as well as basic moieties, and thus can form inner salts or corresponding zwitterions. In general, all pharmaceutically acceptable salt forms of compounds of Formula (I) according to invention including acid addition salts, base addition salts, zwitterions or the like are contemplated to be within the scope of the present invention and are generically referred to as pharmaceutically acceptable salts.

The term "halogen" or "halo" as used herein refers to chlorine, bromine, fluorine, or iodine.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal flora, which is not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, including for example, to increase the solubility of the compound. Typical, non-limiting examples of solid carriers include, starch, lactose, dicalcium phosphate, sucrose, and kaolin and so on. Typical, non-limiting examples of liquid carriers include, sterile water, saline, buffers, non-ionic surfactants, and edible oils such as oil, peanut and sesame oils and so on. In addition, various adjuvants commonly used in the art may be included. These and other such compounds are described in the literature, for example, in the Merck Index (Merck & Company, Rahway, N.J.). Considerations for inclusion of various components in pharmaceutical compositions are described, for example, in Gilman et al. (Eds.) (1990); Goodman and Gilman's: The Pharmacological Basis of Therapeutics, 8th Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salt, pro-drugs, metabolites, esters, ethers, hydrates, polymorphs, solvates, complexes, enantiomers or adducts) which, upon administration to a subject, is capable of providing (directly or indirectly) the antibacterial compound.

In general, the term "cation" includes Na, K, Mg, Ca, $NH_4^+$, $(CH_3CH_2)_3N^+$ etc.

In one general aspect, there are provided compounds of Formula (I):

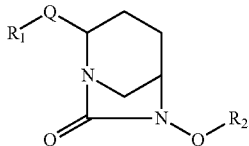

Formula (I)

or a stereoisomer or a pharmaceutically acceptable salt thereof;
wherein:
Q is heteroaryl;
$R_1$ is:
(a) hydrogen,
(b) $(CO)_n$—$R_3$, or
(c) $COOR_4$,
n is 0, 1 or 2;
$R_2$ is:
(a) $SO_3M$,
(b) $SO_2NH_2$,
(c) $PO_3M$,
(d) $CH_2COOM$,
(e) $CF_2COOM$,
(f) $CHFCOOM$, or
(g) $CF_3$;
M is hydrogen or a cation;
$R_3$ is:
(a) hydrogen,
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, $NR_5CONR_6R_7$, heterocyclyl, heteroaryl, cycloalkyl or aryl,
(c) CN,
(d) $NR_6R_7$,
(e) $CONR_6R_7$,
(f) $NHCONR_6R_7$,
(g) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(h) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(i) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(j) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(k) cycloalkyl substituted with $C_1$-$C_6$ alkyl wherein $C_1$-$C_6$ alkyl is further substituted with one or more substituents independently selected from $OR_5$, $NR_6R_7$, halogen, CN, or $CONR_6R_7$, or
(l) $OR_8$;
$R_4$ is:
(a) hydrogen,
(b) $C_1$-$C_6$ alkyl optionally substituted with one or more substituents independently selected from $OR_5$, CN, $COOR_5$, $CONR_6R_7$, $NR_6R_7$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(d) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$,
(e) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$, or
(f) cycloalkyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, or $NHCONR_6R_7$;
$R_5$ and $R_8$ are each independently:
(a) hydrogen, or
(b) $C_1$-$C_6$ alkyl optionally substituted with one or more substituents independently selected from halogen, CN, $CONR_6R_7$, $NR_6R_7$, heterocyclyl, heteroaryl, cycloalkyl or aryl;
$R_6$ and $R_7$ are each independently:
(a) hydrogen,
(b) $C_1$-$C_6$ alkyl optionally substituted with one or more substituents independently selected from halogen, $OR_5$, CN, $COOR_5$, $CONR_5R_8$, $NR_5R_8$, $NR_5COR_8$, heterocyclyl, heteroaryl, cycloalkyl or aryl,
(c) aryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(d) heterocyclyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(e) heteroaryl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$,
(f) cycloalkyl optionally substituted with one or more substituents independently selected from $C_1$-$C_6$ alkyl, $OR_5$, $NR_5R_8$, halogen, CN, $CONR_5R_8$, $SO_2$-alkyl, $SO_2$-aryl, $OSO_2$-alkyl, $OSO_2$-aryl, or $NHCONR_5R_8$, or
(g) $R_6$ and $R_7$ are joined together to form a four to seven member ring.

Typical non-limiting examples of compounds according to the invention include:
trans-sulfuric acid mono-[2-(5-aminomethyl-[1,3,4]-oxadiazol-2-yl)-7-oxo-1,6-diazabicyclo[3.2.1]-octan-6-yl]ester;
trans-sulfuric acid mono-[2-(5-((S)-1-amino-ethyl)-[1,3,4]-oxadiazol-2-yl)-7-oxo-1,6-diazabicyclo[3.2.1]-octan-6-yl]ester;
trans-sulfuric acid mono-[2-(5-((R)-1-amino-ethyl)-[1,3,4]-oxadiazol-2-yl)-7-oxo-1,6-diazabicyclo[3.2.1]-octan-6-yl]ester;
trans-sulfuric acid mono-[2-(5-(piperidin-4-yl)-[1,3,4]-oxadiazol-2-yl)-7-oxo-1,6-diazabicyclo[3.2.1]-octan-6-yl]ester;
trans-sulfuric acid mono-[2-(5-((S)-pyrrolidin-2-yl)-[1,3,4]-oxadiazol-2-yl)-7-oxo-1,6-diazabicyclo[3.2.1]-octan-6-yl]ester;
trans-sulfuric acid mono-[2-(5-(piperazin-1-yl-methyl)-[1,3,4]-oxadiazol-2-yl)-7-oxo-1,6-diazabicyclo[3.2.1]-octan-6-yl]ester;
trans-sulfuric acid mono-[2-(5-((RS)-1-amino-1-phenyl-methyl)-[1,3,4]-oxadiazol-2-yl)-7-oxo-1,6-diazabicyclo[3.2.1]-octan-6-yl]ester;

trans-sulfuric acid mono-[2-(5-(piperidin-4-yl)-[1,2,4]-oxadiazol-3-yl)-7-oxo-1,6-diazabicyclo[3.2.1]-octane;

trans-sulfuric acid mono-[2-(5-((R)-piperidin-3-yl)-[1,3,4]-oxadiazol-2-yl)-7-oxo-1,6-diazabicyclo[3.2.1]-octane;

Sodium salt of trans-6-(sulphooxy)-2-(5-methyl-[1,3,4]-oxadiazol-2-yl)-7-oxo-1,6-diazabicyclo[3.2.1]-octane;

Sodium salt of trans-6-(sulphooxy)-2-(5-ethyl-[1,3,4]-oxadiazol-2-yl)-7-oxo-1,6-diazabicyclo[3.2.1]-octane;

Sodium salt of trans-6-(sulphooxy)-2-(5-trifluoromethyl-[1,3,4]-oxadiazol-2-yl)-7-oxo-1,6-diazabicyclo[3.2.1]-octane;

Sodium salt of trans-6-(sulphooxy)-2-(5-carboxamido-[1,3,4]-oxadiazol-2-yl)-7-oxo-1,6-diazabicyclo[3.2.1]-octane;

Sodium salt of trans-6-(sulphooxy)-2-(5-(isooxazol-3-yl)-[1,3,4]-oxadiazol-2-yl)-7-oxo-1,6-diazabicyclo[3.2.1]-octane;

Sodium salt of trans-6-(sulphooxy)-2-(5-(furan-2-yl)-[1,3,4]-oxadiazol-2-yl)-7-oxo-1,6-diazabicyclo[3.2.1]-octane;

Sodium salt of trans-6-(sulphooxy)-2-(5-phenyl-[1,3,4]-oxadiazol-2-yl)-7-oxo-1,6-diazabicyclo[3.2.1]-octane;

Sodium salt of trans-6-(sulphooxy)-2-(5-(pyridin-2-yl)-[1,3,4]-oxadiazol-2-yl)-7-oxo-1,6-diazabicyclo[3.2.1]-octane;

Sodium salt of trans-6-(sulphooxy)-2-(5-(6-carboxamido-pyridin-2-yl)-[1,3,4]-oxadiazol-2-yl)-7-oxo-1,6-diazabicyclo[3.2.1]-octane;

Sodium salt of trans-6-(sulphooxy)-2-(5-(5,6-dihydro-8H-imidazo[2,1-c][1,4]-oxazin-2-yl)-[1,3,4]-oxadiazol-2-yl)-7-oxo-1,6-diazabicyclo[3.2.1]-octane;

Sodium salt of trans-6-(sulphooxy)-2-(5-(morpholino-4-methyl)-[1,3,4]-oxadiazol-2-yl)-7-oxo-1,6-diazabicyclo[3.2.1]-octane;

Sodium salt of trans-sulfuric acid mono-[2-(5-(morpholin-4-yl-carbonyl)-[1,3,4]-oxadiazol-2-yl)-7-oxo-1,6-diazabicyclo[3.2.1]-octan-6-yl]ester;

Sodium salt of trans-6-(sulphooxy)-2-(5-methyl-[1,3,4]-thiadiazol-2-yl)-7-oxo-1,6-diazabicyclo[3.2.1]-octane;

Sodium salt of trans-6-(sulphooxy)-2-(5-methyl-[1,2,4]-oxadiazol-3-yl)-7-oxo-1,6-diazabicyclo[3.2.1]-octane;

Sodium salt of trans-6-(sulphooxy)-2-(5-ethoxycarbonyl-[1,2,4]-oxadiazol-3-yl)-7-oxo-1,6-diazabicyclo[3.2.1]-octane;

Sodium salt of trans-6-(sulphooxy)-2-(2-methyl-2H-[1,2,3,4]-tetrazol-5-yl)-7-oxo-1,6-diazabicyclo[3.2.1]-octane;

Sodium salt of trans-6-(sulphooxy)-2-(1-methyl-1H-[1,2,3,4]-tetrazol-5-yl)-7-oxo-1,6-diazabicyclo[3.2.1]-octane;

Sodium salt of trans-6-(sulphooxy)-2-(3-ethoxycarbonyl-[1,2,4]-oxadiazol-5-yl)-7-oxo-1,6-diazabicyclo[3.2.1]-octane;

Sodium salt of trans-6-(sulphooxy)-2-(5-carboxamido-[1,2,4]-oxadiazol-3-yl)-7-oxo-1,6-diazabicyclo[3.2.1]-octane;

or a stereoisomer or a pharmaceutically acceptable salt thereof.

In general, the compounds of the invention can be prepared according to the following procedures. A person of skills in the art would appreciate that the described methods can be varied or optimized further to provide the desired and related compounds. In the following procedures, all variables are as defined above.

(A) Synthesis of Compounds Containing 1,3,4-Oxadiazole Groups:

In general the compounds according to the invention containing 1,3,4-Oxadiazole groups were prepared using a procedure given in Scheme 1.

Typically, trans-6-benzyloxy-7-oxo-1,6-diaza-bicyclo[3.2.1]octane-2-carboxylic acid (1a, which is disclosed in WO 2009/091856 A2), was reacted with alkyl or aryl or suitably substituted aryl or alkyl acid hydrazides in the presence of a suitable coupling agent (for example, EDC hydrochloride, dicyclohexylcarbodiimide (DCC), or pivalyl chloride) in a suitable solvent (for example, N,N dimethyl formamide, N,N dimethyl acetamide, 1,4 dioxane or chloroform), and in the presence of a suitable base (for example, N-methyl morpholine, triethylamine or diisopropyl ethyl-amine), and N-hydroxybenzotriazole (HOBt) at a temperature ranging from about −15° C. to 60° C., for about 1 to 24 hours to provide intermediate compound (1b).

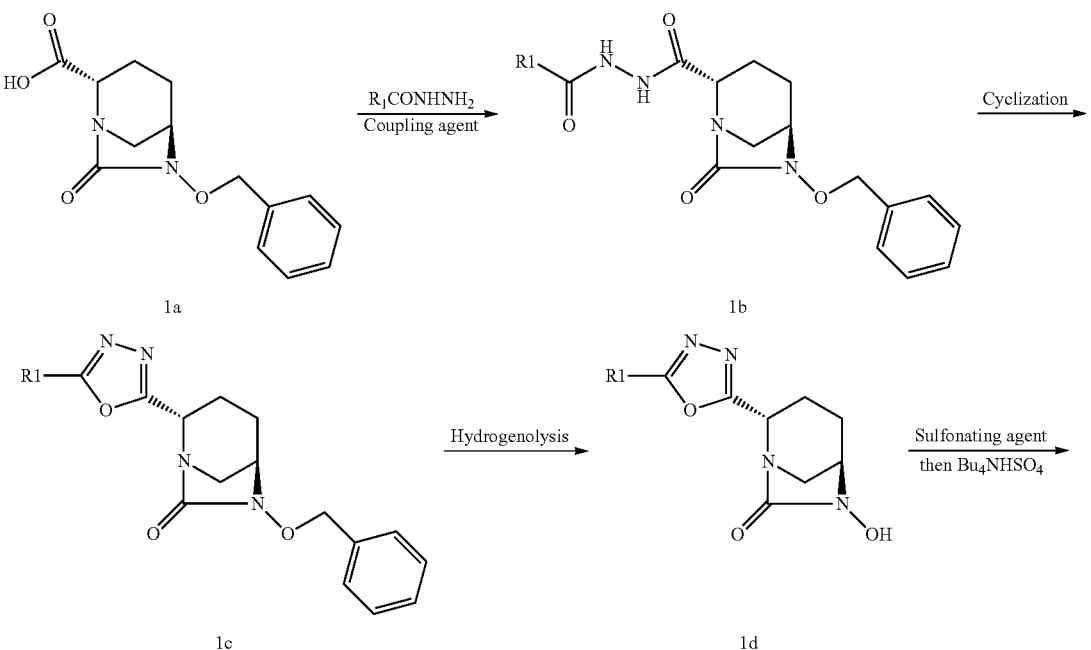

Scheme-1

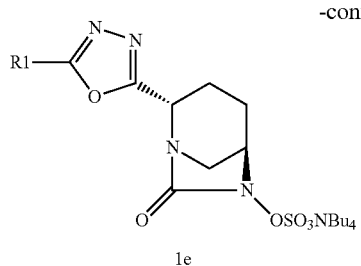

1e

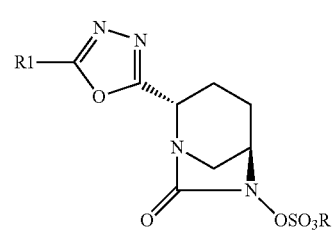

R = H when R1 bears amine group or;
R = Na

CF₃COOH
(when R contains
t-Boc—NH or
alkyl silyloxy group)

The cyclization of intermediate compound (1b) was effected by treating intermediate compound (1b) with a suitable reagent such as p-toluene sulfonyl chloride, p-nitrobenzene sulfonyl chloride, or methane sulfonyl chloride, in a suitable solvent (for example, toluene, chloroform, dichloromethane, or N,N-dimethyl formamide), at a temperature ranging from 25° C. to 110° C. for about 1 to 24 hours to obtain 1,3,4-oxadiazole intermediate compound (1c). Alternatively, the intermediate compound (1c) may also be prepared by refluxing intermediate compound (1b) in toluene in presence of 4° A molecular sieves.

The 1,3,4-oxadiazole intermediate compound (1c) was subjected for hydrogenolysis by using a suitable catalyst (for example, 5% or 10% palladium on carbon or 20% palladium hydroxide on carbon), in presence of a suitable hydrogen source (for example, hydrogen gas, ammonium formate, or cyclohexene) in a suitable solvent (for example, methanol, ethanol, methanol-dichloromethane mixture, or N,N dimethyl formamide-dichloromethane mixture) at a temperature ranging from about 25° C. to 60° C. for about 1 to 24 hours to obtain intermediate compound (1d).

The intermediate compound (1d) was sulfonated by reacting it with a suitable sulfonating reagent (for example, pyridine sulfur trioxide complex or N,N-dimethyl formide sulfur trioxide complex) in a suitable solvent (for example, pyridine, N,N-dimethyl formamide, dichlromethane or mixture thereof) at a temperature ranging from about 25° C. to 80° C. for about 1 to 24 hours to provide pyridine salt of sulfonic acid which was subsequently treated with tetrabutyl ammonium sulfate to provide terabutylammonium salt of sulfonic acid intermediate compound (1e).

Some compounds of the invention were isolated as a sodium salt by passing intermediate compound (1e) through sodium form of Aberlite 200 C resin in aqueous tetrahydrofuran followed by evaporation of solvent fractions under vacuum.

Some other compounds, when R contains tert-butoxycarbonyl group or alkylsilyl group, were isolated as zwitterions by treating intermediate compound (1e) with trifluoroacetic acid in the absence of solvent or in the presence of the solvent (for example, dichloromethane, chloroform, or acetonitrile) at a temperature ranging from about -10° C. to 40° C., for about 1 to 14 hours.

(B) Synthesis of Compounds Containing 1,3,4-Thiadiazole Groups:

In general, the compounds according to the invention containing 1,3,4-Thiadiazole were prepared using a general procedure described in Scheme 2.

Scheme-2

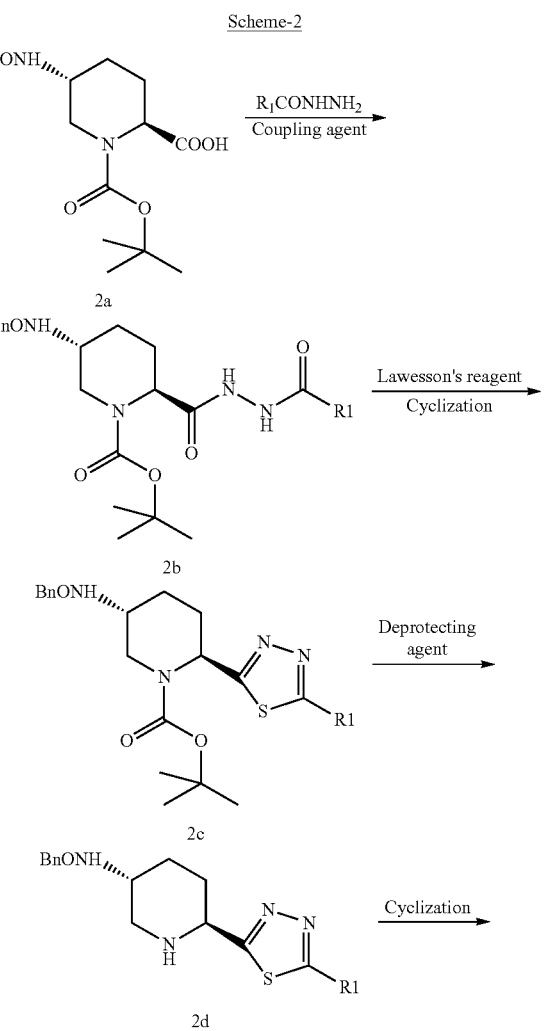

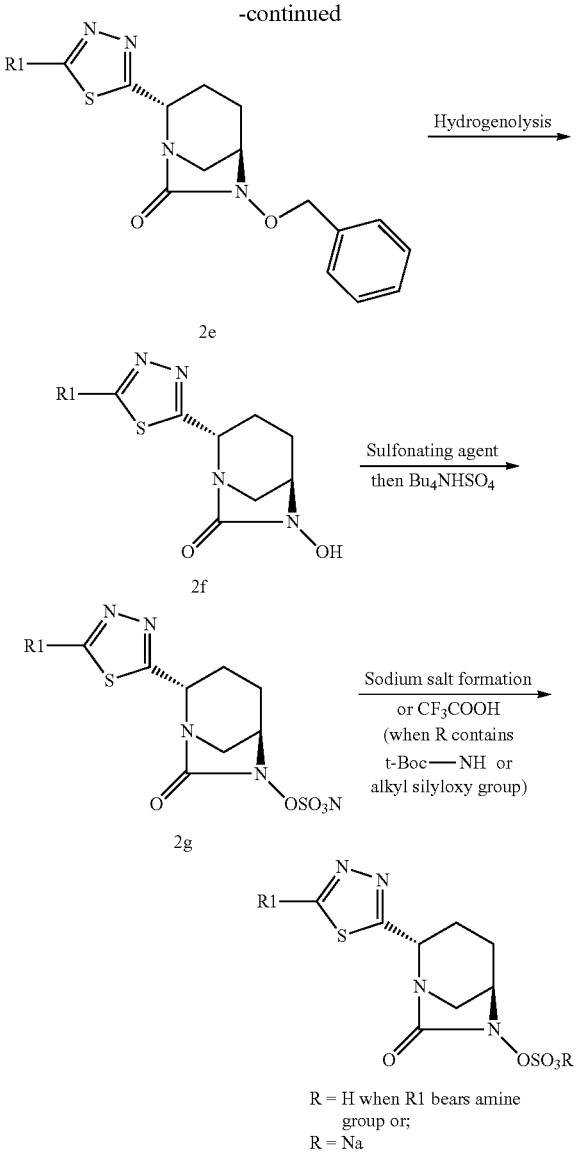

As per Scheme-2, trans-5-benzyloxyamino-piperidine-1,2-dicarboxylic acid-1-tert-butyl ester (2a), was reacted with alkyl or aryl or suitably substituted aryl or alkyl acid hydrazides in presence of a suitable coupling agent (for example, EDC hydrochloride, dicyclohexylcarbodiimide (DCC), or pivalyl chloride), in a suitable solvent (for example, N,N dimethyl formamide, N,N dimethyl acetamide, 1,4 dioxane or chloroform), in presence of a suitable base (for example, N-methyl morpholine, triethylamine or diisopropyl ethylamine and N-hydroxybenzotriazole (HOBt)) at a temperature ranging from about −5° C. to 60° C. for about 1 to 24 hours to provide intermediate compound (2b).

The cyclization of intermediate compound (2b) was effected by treating intermediate compound (2b) with Lowesson's reagent, in a suitable solvent (for example, toluene, chloroform, tetrahydrofuran, or N,N-dimethyl formamide) at a temperature ranging from 25° C. to 110° C., for about 1 to 24 hours to provide 1,3,4-thiadiazole intermediate compound (2c).

The intermediate compound (2c) was deprotected to provide intermediate compound (2d), using deprotecting agent such as trifluoro acetic acid or hydrochloric acid in a solvent such as dichloromethane, chloroform, acetonitrile, or water at a temperature ranging from about −5° C. to 50° C. for about 1 to 24 hours.

The cyclization of intermediate compound (2d) was achieved by treating intermediate compound (2d) using a suitable reagent (for example, phosgene solution, diphosgene or triphosgene) in a suitable solvent (for example, toluene, chloroform, acetonitrile and in presence of a suitable base (for example, triethyl amine, or diisopropyl ethyl amine, N,N-dimethylamino pyridine) at a temperature ranging from about −5° C. to 50° C. for about 1 to 24 hours to provide cyclized intermediate compound (2e).

The cyclized intermediate compound (2e) was subjected for hydrogenolysis by using a suitable catalyst (for example, 5% or 10% palladium on carbon, or 20% palladium hydroxide on carbon) in presence of a suitable hydrogen source (for example, hydrogen gas, ammonium formate, or cyclohexene) in a suitable solvent (for example, methanol, ethanol, methanol-dichloromethane mixture, or N,N dimethyl formamide dichloromethane mixture), at a temperature ranging from 25° C. to 60° C. for about 1 to 24 hours to provide N-hydroxy intermediate compound (2f).

The intermediate compound (2f) was sulfonated by reacting it with a suitable sulfonating reagent (for example, pyridine sulfur trioxide complex, or N,N-dimethyl formamide sulfur trioxide complex) in a suitable solvent (for example, pyridine, N,N-dimethyl formamide, dichloromethane or mixture thereof) at a temperature ranging from about 0° C. to 50° C. for about 1 to 24 hours to provide pyridine salt of sulfonic acid which was subsequently treated with tetrabutyl ammonium acetate to provide terabutylammonium salt of sulfonic acid intermediate compound (2g).

The compound of invention was isolated as a sodium salt by passing intermediate compound (2g) through sodium form of Aberlite SR-L resin in aqueous tetrahydrofuran followed by evaporation of solvent fractions under vacuum. Alternatively, when R contains tert-butoxycarbonyl group or alkylsilyl group, then compound of invention was isolated as zwitterions by treating intermediate compound (2g) with trifluoroacetic acid in absence of solvent or in the presence of a suitable solvent (for example, dichloromethane, chloroform, or acetonitrile) at a temperature ranging from about −10° C. to 40° C. for about 1 to 14 hours.

(C) Synthesis of Compounds Containing 1,2,4-Oxadiazol-3-yl Groups:

In general, the compound according to the invention containing 1,2,4-Oxadiazol-3-yl groups was prepared using a general procedure described in Scheme 3.

As per Scheme-3, trans-5-benzyloxyamino-piperidine-1,2-dicarboxylic acid-1-tert-butyl ester compound (2a), was reacted with a suitable acid chloride (for example, pivolyl chloride) in presence of a suitable base (for example, N-methyl morpholine, triethylamine, diisopropyl ethylamine) in a suitable solvent (for example, dichloromethane, tetrahydrofuran, 1,4 dioxane or chloroform), at a temperature ranging from about −5° C. to 35° C., for about 1 to 2 hours to provide anhydride which was subsequently treated with ammonia gas at a temperature ranging from about −50° C. to 5° C. for about 0.5 to 2 hours to provide amide intermediate compound (3b).

Dehydration of the intermediate compound (3b) was effected by treating intermediate (3b) with trifluoroacetic anhydride, in a suitable solvent (for example, toluene, chloroform, tetrahydrofuran, or dichloromethane), at a temperature ranging from about −5° C. to 35° C., for about 1 to 24 hours to provide the nitrile intermediate compound (3c).

The intermediate compound (3c) was reacted with hydroxylamine hydrochloride in a suitable solvent (for example, methanol, water, ethanol, or mixture thereof), at a temperature ranging from about −5° C. to 35° C., for about 1 to 24 hours to provide the amidoxime intermediate compound (3d).

The intermediate compound (3d) was reacted with suitably substituted alkyl anhydride in a suitable solvent (for example, dichloromethane, chloroform, tetrahydrofuran, or mixture thereof), and in presence of a suitable base (for example, N-methyl morpholine, triethylamine, or diisopropyl ethylamine) at a temperature ranging from about −5° C. to 35° C., for about 1 to 24 hours to provide the O-acylated amidoxime intermediate compound (3e).

Cyclization of the intermediate compound (3e) was affected by refluxing intermediate compound (3e) in pyridine for about 1 to 24 hours to provide the cyclized intermediate compound (3f).

The intermediate compound (3f) was deprotected to provide intermediate compound (3g), using a suitable deprotecting agent (for example, trifluoro acetic acid, or hydrochloric acid) in a suitable solvent (for example, dichloromethane, chloroform, acetonitrile or water), at a temperature ranging from about −25° C. to 50° C. for about 1 to 24 hours.

The cyclization of intermediate compound (3g) was achieved by treating intermediate compound (3g) with a suitable reagent (for example, phosgene solution, diphosgene or triphosgene) in a suitable solvent (for example, toluene, chloroform, or acetonitrile), and in presence of a suitable base (for example, triethyl amine or diisopropyl ethyl amine) at a temperature ranging from about −5° C. to 50° C. for about 1 to 24 hours to provide the cyclized intermediate compound (3h).

The cyclized intermediate compound (3h) was subjected for hydrogenolysis using a suitable catalyst (for example, 5% or 10% palladium on carbon, or 20% palladium hydroxide on carbon) in presence of a suitable hydrogen source (for example, hydrogen gas, ammonium formate, or cyclohexene) in a suitable solvent (for example, methanol, ethanol, methanol-dichloromethane mixture, or N,N dimethyl formamide dichloromethane mixture) at a temperature ranging from about 25° C. to 60° C., for about 1 to 24 hours to provide N-hydroxy intermediate compound (3i).

The intermediate compound (3i) was sulfonated by reacting it with a suitable sulfonating reagent (for example, pyridine sulfur trioxide complex, or N,N-dimethyl formamide sulfur trioxide complex) in a suitable solvent (for example, pyridine, N,N-dimethyl formamide, dichloromethane or a mixture thereof), at a temperature ranging from about −5° C. to 50° C., 0.5 to 24 hours to provide pyridine salt of sulfonic acid which subsequently was treated with tetrabutyl ammonium acetate to provide terabutylammonium salt of sulfonic acid intermediate compound (3j).

The compound of the invention was isolated as a sodium salt by passing intermediate compound (3j) through sodium form of Dowex 50WX8 200 resin in aqueous tetrahydrofuran followed by evaporation of solvent fractions under vacuum.

Alternatively, when R contains tert-butoxycarbonyl group or alkylsilyl group then compound of the invention was isolated as zwitterions by treating intermediate compound (3j) with trifluoroacetic acid in the absence of solvent or in the presence of the solvent (for example, dichloromethane, chloroform, or acetonitrile) at a temperature ranging from −10° C. to 40° C. for about 1 to 14 hours.

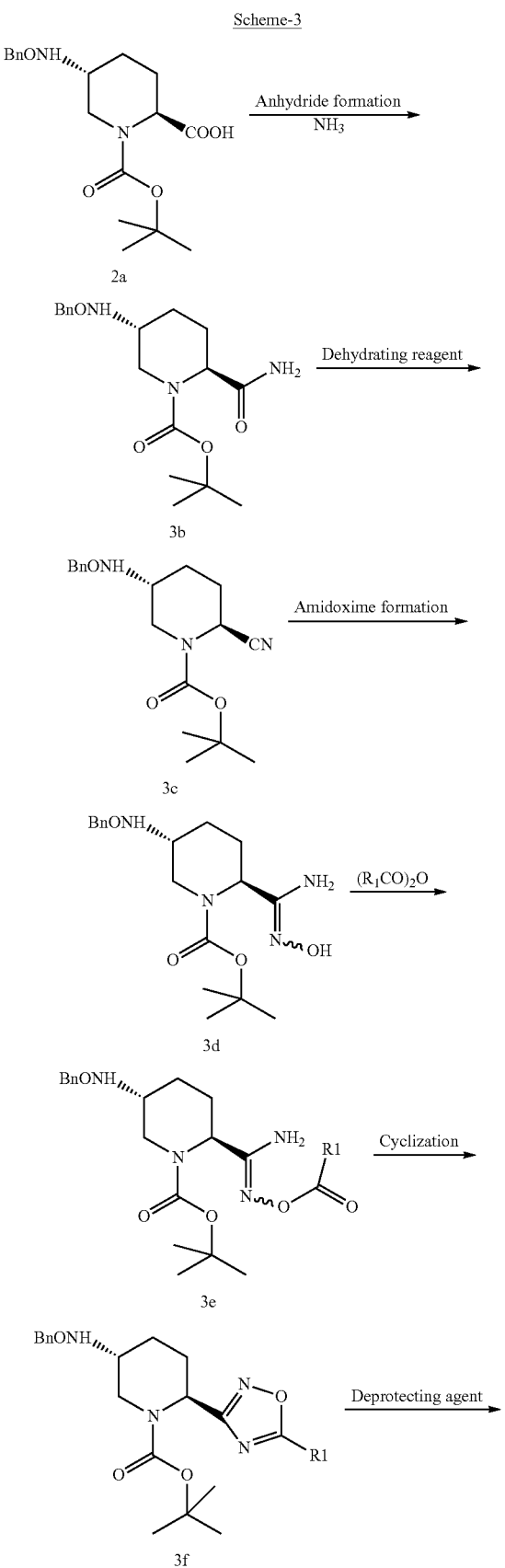

Scheme-3

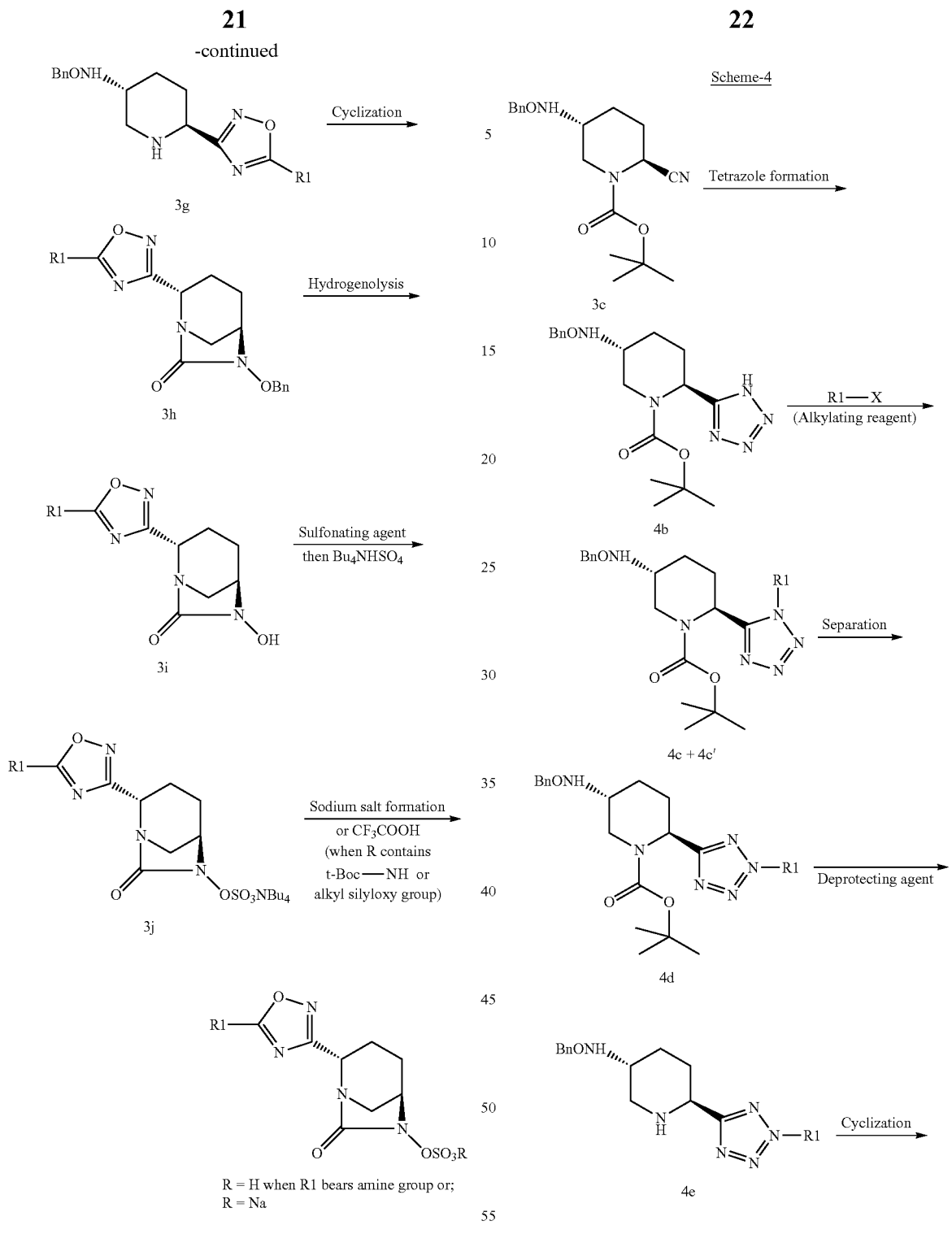

(D) Synthesis of Compounds Containing 1,2,3,4-Tetrazol Groups:

As per Scheme-4, trans-5-benzyloxyamino-2-cyano-piperidine-1-carboxylic acid-1-tert-butyl ester compound (3c), was reacted sodium azide in presence of triethylamine hydrochloride, in a suitable solvent (for example, toluene, or xylene) at a reflux temperature for about 1 to 12 hours to provide tetrazole intermediate compound (4b).

-continued

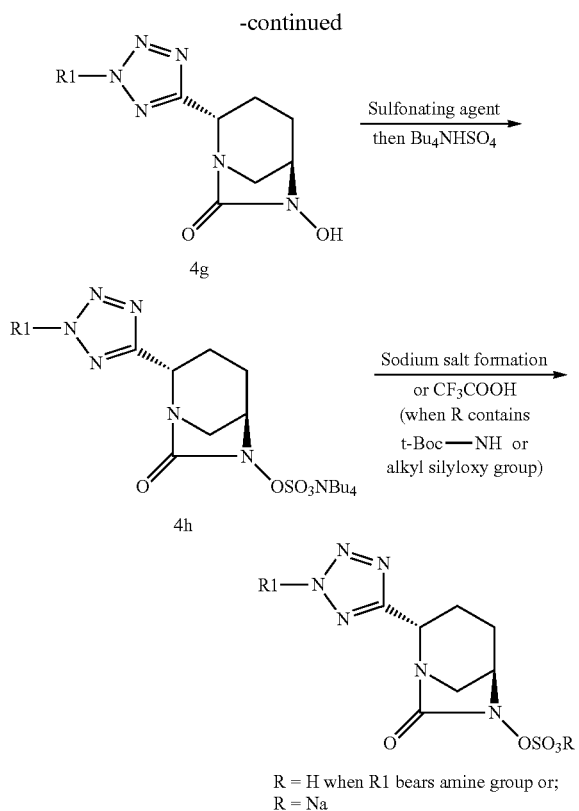

4g

4h

R = H when R1 bears amine group or;
R = Na

Alkylation of the intermediate compound (4b) was effected by treating intermediate compound (4b) with suitable alkyl halide in a suitable solvent (for example, N,N-dimethyl formamide, N,N-dimethyl acetamide, tetrahydrofuran) and in the presence of a suitable base (for example, cesium carbonate, potassium carbonate or sodium carbonate) at a temperature ranging from about −5° C. to 35° C. for about 1 to 24 hours to provide isomeric mixture of N-alkyl tetrazol intermediate compounds (4c) and (4c'), which was separated using column chromatography technique to provide isomerically pure compound (4c) and (4c') and hitherto the pure intermediate is referred as compound (4d).

The intermediate compound (4d) was deprotected to provide intermediate compound (4e), using a suitable deprotecting agent (trifluoro acetic acid or hydrochloric acid), in a suitable solvent (for example, dichloromethane, chloroform, acetonitrile or water), at a temperature ranging from about −25° C. to 50° C., for about 1 to 24 hours.

The cyclization of intermediate compound (4e) was achieved by treating intermediate compound (4e) using a suitable reagent (for example, phosgene solution, diphosgene or triphosgene) in a suitable solvent (for example, toluene, chloroform, or acetonitrile) in the presence of a suitable base (for example, triethyl amine or diisopropyl ethyl amine) and N,N-dimethylamino pyridine at a temperature ranging from about −5° C. to 50° C. for about 1 to 24 hours to provide cyclized intermediate compound (4f).

The cyclized intermediate compound (4f) was subjected for hydrogenolysis by using a suitable catalyst (for example, 5% or 10% palladium on carbon or 20% palladium hydroxide on carbon) in presence of a suitable hydrogen source (for example, hydrogen gas, ammonium formate, or cyclohexene) in a suitable solvent (for example, methanol, ethanol, methanol-ethyl acetate mixture, or N,N dimethyl formamide-dichloromethane mixture) at a temperature ranging from about 25° C. to 60° C., for 1 to 24 hours to provide N-hydroxy intermediate compound (4g).

The intermediate compound (4g) was sulfonated by reacting it with a suitable sulfonating reagent such (for example, pyridine sulfur trioxide complex, or N,N-dimethyl formamide sulfur trioxide complex) in a suitable solvent (for example, pyridine, N,N-dimethyl formamide, dichloromethane or mixture thereof) at a temperature ranging from about −5° C. to 50° C. for about 0.5 to 24 hours to provide pyridine salt of sulfonic acid which subsequently was treated with tetrabutyl ammonium acetate to provide terabutylammonium salt of sulfonic acid intermediate compound (4h).

The compound of invention was isolated as a sodium salt by passing intermediate 4h through sodium form of Dowex 50WX8 200 resin in aqueous tetrahydrofuran followed by evaporation of solvent fractions under vacuum. Alternatively, when R contains tert-butoxycarbonyl group or alkylsilyl group then compound of invention was isolated as zwitterions by treating intermediate 4h with trifluoroacetic acid in the absence of solvent or in the presence of a suitable solvent (for example, dichloromethane, chloroform, or acetonitrile) at a temperature ranging from about −10° C. to 40° C. for about 1 to 14 hours.

(E) Synthesis of Compounds Containing 1,2,4-Oxadiazol-5-yl Groups:

In general, the compounds according to the invention containing 1,2,4-Oxadiazol-5-yl groups were prepared using a general procedure described in Scheme 5.

As per Scheme-5, trans-6-benzyloxy-7-oxo-1,6-diaza-bicyclo[3.2.1]octane-2-carboxylic acid compound (1a), was reacted with suitably substituted aryl or alkyl amidoxime in the presence of a suitable coupling agent (for example, EDC hydrochloride, dicyclohexylcarbodiimide (DCC), or pivalyl chloride) in a suitable solvent (for example N,N dimethyl formamide, N,N dimethyl acetamide, 1,4 dioxane or chloroform) and in presence of a suitable base (for example, N-methyl morpholine, triethylamine or diisopropyl ethylamine) and N-hydroxybenzotriazole (HOBt) at a temperature ranging from about −5° C. to 60° C., for about 1 to 24 hours to provide intermediate compound (5b).

Scheme-5

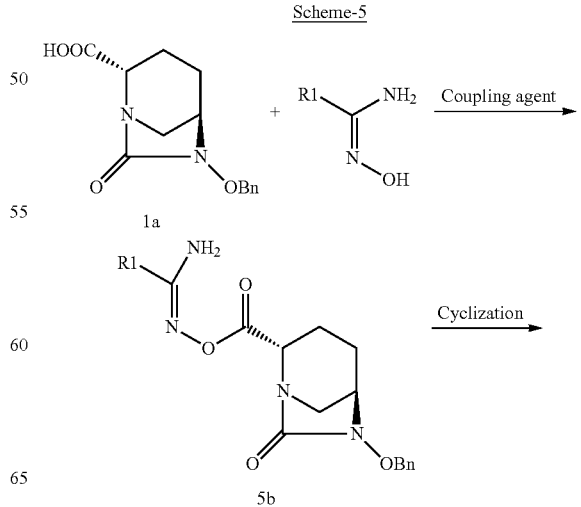

5b

-continued

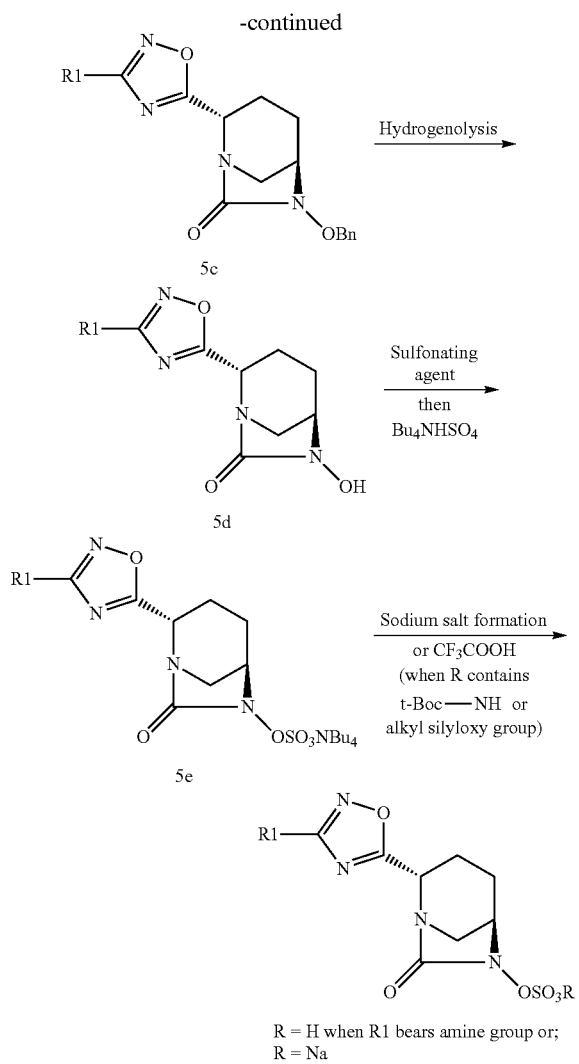

R = H when R1 bears amine group or;
R = Na

The cyclization of intermediate compound (5b) was achieved by refluxing intermediate compound (5b) in pyridine for about 1 to 24 hours to provide cyclized intermediate compound (5c).

The cyclized intermediate compound (5c) was subjected for hydrogenolysis by using a suitable catalyst (for example, 5% or 10% palladium on carbon, or 20% palladium hydroxide on carbon) in presence of a suitable hydrogen source (for example, hydrogen gas, ammonium formate, or cyclohexene) in a suitable solvent (for example, methanol, ethanol, methanol-ethyl acetate mixture, N,N dimethyl formamide dichloromethane mixture) at a temperature ranging from about 25° C. to 60° C. for about 1 to 24 hours to provide N-hydroxy intermediate compound (5d).

The intermediate compound (5d) was sulfonated by reacting it with a suitable sulfonating reagent (for example, pyridine sulfur trioxide complex, or N,N-dimethyl formamide sulfur trioxide complex) in a suitable solvent (for example, pyridine, N,N-dimethyl formamide, dichloromethane or a mixture thereof) at a temperature ranging from about −5° C. to 50° C. for about 0.5 to 24 hours to provide pyridine salt of sulfonic acid which subsequently was treated with tetrabutyl ammonium acetate to provide terabutylammonium salt of sulfonic acid intermediate compound (5e).

The compound of invention was isolated as a sodium salt by passing intermediate 5e through sodium form of Amberlite 200 C resin in aqueous tetrahydrofuran followed by evaporation of solvent fractions under vacuum. Alternatively, when R contains tert-butoxycarbonyl group or alkylsilyl group then compound of invention was isolated as zwitterions by treating intermediate (5e) with trifluoroacetic acid in the absence of solvent or in the presence of a suitable solvent (for example, dichloromethane, chloroform, or acetonitrile) at a temperature ranging from about −10° C. to 40° C. for about 1 to 14 hours.

In some embodiments, there are provided pharmaceutical compositions comprising a compound of Formula (I), or a stereoisomer or a pharmaceutically acceptable salt thereof.

In some other embodiments, there is provided a method for preventing or treating bacterial infection in a subject, said method comprising administering to said subject a pharmaceutically effective amount of a compound of Formula (I) or a stereoisomer or a pharmaceutically acceptable salt thereof.

In some embodiments, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In some other embodiments, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In some embodiments, there are provided pharmaceutical compositions comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In some other embodiments, there are provided pharmaceutical compositions comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one beta-lactamase inhibitor selected from sulbactam, tazobactam, clavulanic acid, or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, and (b) at least one antibacterial agent or a pharmaceutically acceptable derivative thereof.

In some other embodiments, there is provided a method for preventing or treating bacterial infection in a subject, said method comprising administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some other embodiments, there is provided a method for preventing or treating a bacterial infection in a subject, said infection being caused by bacteria producing one or more beta-lactamase enzymes, wherein the method comprises administering to said subject a pharmaceutically effective amount of: (a) a compound of Formula (I), or a stereoisomer or a pharmaceutically acceptable salt thereof, (b) at least one beta-lactamase inhibitor selected from sulbactam, tazobactam, clavulanic acid, or a pharmaceutically acceptable derivative thereof, and (c) at least one antibacterial agent or a pharmaceutically acceptable derivative thereof.

In some embodiments, there are provided methods for increasing antibacterial effectiveness of a antibacterial agent in a subject, said method comprising co-administering said antibacterial agent or a pharmaceutically acceptable derivative thereof with a pharmaceutically effective amount of a compound of Formula (I) or a stereoisomer or a pharmaceutically acceptable salt thereof.

In some embodiments, the compositions and methods according to the invention use compounds of Formula (I) or a stereoisomer or a pharmaceutically acceptable salt thereof in combination with at least one antibacterial agent or a pharmaceutically acceptable derivative thereof. A wide variety of antibacterial agents can be used. Typical, non-limiting examples of antibacterial agents include one or more of antibacterial compounds generally classified as aminoglycosides, Ansamycins, Carbacephems, Cephalosporins, Cephamycins, Lincosamides, Lipopeptides, Macrolides, Monobactams, Nitrofurans, Penicillins, Polypeptides, Quinolones, Sulfonamides, Tetracyclines, Oxazolidinone and the like.

Typical, non-limiting examples of Aminoglycoside antibacterial agents include Amikacin, Gentamicin, Kanamycin, Neomycin, Netilmicin, Tobramycin, Paromomycin, Arbekacin, Streptomycin, Apramycin and the like.

Typical, non-limiting examples of Ansamycin antibacterial agents include Geldanamycin, Herbimycin and the like.

Typical, non-limiting examples of Carbacephem antibacterial agents include Loracarbef and the like.

Typical, non-limiting examples of Carbapenem antibacterial agents include Ertapenem, Doripenem, Imipenem, Meropenem and the like.

Typical, non-limiting examples of Cephalosporin and Cephamycin antibacterial agents include Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cephamycin, Cefoxitin, Cefotetan, Cefmetazole, Carbacephem, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftobiprole, Ceftiofur, Cefquinome, Cefovecin, CXA-101, Ceftaroline, Ceftobiprole etc.

Typical, non-limiting examples of Lincosamide antibacterial agents include Clindamycin, Lincomycin and the like.

Typical, non-limiting examples of Macrolide antibacterial agents include Azithromycin, Clarithromycin, Dirithromycin, Erythromycin, Roxithromycin, Troleandomycin, Telithromycin, Spectinomycin, Solithromycin and the like.

Typical, non-limiting examples of Monobactam antibacterial agents include Aztreonam and the like.

Typical, non-limiting examples of Nitrofuran antibacterial agents include Furazolidone, Nitrofurantoin and the like.

Typical, non-limiting examples of Penicillin antibacterial agents include Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin and the like.

Typical, non-limiting examples of Polypeptide antibacterial agents include Bacitracin, Colistin, Polymyxin B and the like.

Typical, non-limiting examples of Quinolone antibacterial agents include Ciprofloxacin, Enoxacin, Gatifloxacin, Levofloxacin, Lomefloxacin, Moxifloxacin, Nalidixic acid, Levonadifloxacin, Norfloxacin, Ofloxacin, Trovafloxacin, Grepafloxacin, Sparfloxacin, Temafloxacin and the like.

Typical, non-limiting examples of Sulfonamide antibacterial agents include Mafenide, Sulfonamidochrysoidine, Sulfacetamide, Sulfadiazine, Sulfamethizole, Sulfamethoxazole, Sulfasalazine, Sulfisoxazole, Trimethoprim and the like.

Typical, non-limiting examples of Tetracycline antibacterial agents include Demeclocycline, Doxycycline, Minocycline, Oxytetracycline, Tetracycline, Tigecycline and the like.

Typical, non-limiting examples of Oxazolidinone antibacterial agents include Tedizolid, Linezolid, Ranbezolid, Torezolid, Radezolid etc.

The pharmaceutical compositions according to the invention may include one or more pharmaceutically acceptable carriers or excipients or the like, Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) ore are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered be less or not susceptible to one or more of known antibacterial agents or their known compositions. Some non-limiting examples of such bacteria known to have developed resistance to various antibacterial agents include Acinetobacter, E. coli, Pseudomonas aeruginosa, Staphylococcus aureus, Enterobacter, Klebsiella, Citrobacter and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibiotics represents a significant improvement in the art.

In general, the compounds of Formula (I) or a stereoisomer or pharmaceutically acceptable salt thereof according to invention are also useful in increasing antibacterial effectiveness of a antibacterial agent in a subject. The antibacterial effectiveness of one or more antibacterial agents may increased, for example, by co-administering said antibacterial agent or a pharmaceutically acceptable salt thereof with a pharmaceutically effective amount of a compound of Formula (I) or a stereoisomer or a pharmaceutically acceptable salt thereof according to the invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1

Sodium salt of trans-6-(sulphooxy)-2-(5-methyl-[1,3,4]-oxadiazol-2-yl)-7-oxo-1,6-diazabicyclo[3.2.1]-octane

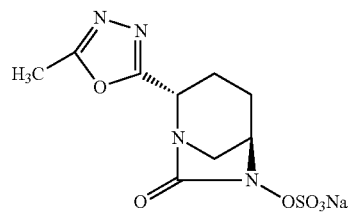

Step-1: Preparation of trans-6-benzyloxy-7-oxo-1,6-diaza-bicyclo[3.2.1]octane-2-carboxylic acid N'-acetyl hydrazide To a mixture of acetic acid hydrazide (1.47 gm, 19.9 mmol) and trans-6-benzyloxy-7-oxo-1,6-diaza-bicyclo [3.2.1]octane-2-carboxylic acid (5 gm, 18.1 mmol) in N,N-dimethyl formamide (50 ml), was added EDC hydrochloride (5.19 gm, 27.1 mmol), DIPEA (9.50 ml, 54.3 mmol) and HOBt (3.66 gm, 27.1 mmol). The reaction mixture was stirred at a temperature between 25° C. to 35° C. for 14 hours. It was diluted with water (250 ml) and extracted with ethyl acetate (75 ml×3). The combined organic extract was washed with water, saturated aqueous sodium chloride solution (100 ml) and layers were separated. The organic layer was concentrated in vacuum to provide the crude compound, which was subjected for silica gel column chromatography using methanol chloroform to provide Step-1 product (2.2 gm) in 33% yield as powder.

Analysis:

MS (ES+) $C_{16}H_{20}N_4O_4$=333.2 (M+1);

$H^1$NMR (CDCl$_3$)=8.52 (s, 1H), 7.67 (s, 1H), 7.35-7.43 (m, 5H), 5.05 (d, 1H), 4.91 (d, 1H), 4.01 (d, 1H), 3.21 (br d, 1H), 3.04-3.15 (m, 2H), 2.30-2.35 (m, 1H), 2.02 (s, 3H), 1.89-2.05 (m, 3H).

Step-2: Preparation of trans-6-benzyloxy-2-(5-methyl-[1,3,4]-oxadiazol-2-yl)-7-oxo-1,6-diazabicyclo[3.2.1]-octane The product as obtained in Step-1 (2 gm, 6.0 mmol) in chloroform (30 ml) was added diisopropylethylamine (3 ml, 17.4 mmol) followed by p-toluene sulfonyl chloride (1.72 gm, 9.0 mmol). The reaction mixture was refluxed until TLC showed complete consumption of starting material. As the reaction was completed, the water (50 ml) was added, and the mixture was extracted with chloroform (50 ml×2) and layers were separated. The organic layer was concentrated in vacuum to provide crude compound that was subjected to silica gel column chromatography to provide cyclized Step-2 product as a powder (1.25 gm) in 80% yield.

Analysis:
MS (ES+) $C_{16}H_{18}N_4O_3$=315.2 (M+1);
H$^1$NMR (CDCl$_3$)=7.25-7.44 (m, 5H), 4.08 (d, 1H), 4.23 (d, 1H), 4.69 (t, 1H), 3.36 (br t, 1H), 2.90-2.94 (m, 1H), 2.80 (d, 1H), 2.54 (s, 3H), 2.26-2.31 (m, 2H), 2.10-2.12 (m, 1H), 1.94-1.98 (m, 1H).

Step-3: Preparation of trans-6-hydroxy-2-(5-methyl-[1,3,4]-oxadiazol-2-yl)-7-oxo-1,6-diazabicyclo[3.2.1]-octane The Step-2 product (1.2 gm, 3.8 mmol) and 10% palladium on carbon (300 mg) in methanol (25 ml) was stirred under atmospheric hydrogen pressure at a temperature of 30° C. for 4 hours. As TLC indicated completion of reaction, the catalyst was filtered over a celite bed and catalyst-containing bed was washed with additional methanol. The filtrate was concentrated in vacuum to provide a white powder compound in 0.82 gm quantity as a Step-3 product in 80% yield.
Analysis:
MS (ES+) $C_9H_{12}N_4O_3$=225.1 (M+1);
H$^1$NMR (DMSO-d$^6$)=9.84 (s, 1H), 4.54 (d, 1H), 3.63 (br s, 1H), 2.92 (br d, 1H), 2.69 (d, 1H), 2.48 (s, 3H), 1.98-2.16 (m, 3H), 1.81-1.88 (m, 1H).

Step-4: Preparation of tetrabutylammonium salt of trans-6-sulphooxy-2-(5-methyl-[1,3,4]-oxadiazol-2-yl)-7-oxo-1,6-diazabicyclo[3.2.1]-octane Product as obtained in Step-3 (0.82 gm, 3.66 mmol) was dissolved in pyridine (8.2 ml) and to the clear solution was added pyridine sulfur trioxide complex (2.91 gm, 18.3 mmol). The suspension was stirred at a temperature of 35° C. for overnight. The suspension was filtered and the solids were washed with dichloromethane (10 ml×2). The filtrate was evaporated under vacuum and the residue was dissolved in 0.5N aqueous potassium dihydrogen phosphate solution (50 ml) for 0.5 hour. The solution was washed with dichloromethane (30 ml) and layers were separated. To the aqueous layer was added tetrabutylammonium sulphate (1.23 gm, 3.66 mmol) and stirred for two hours at 25° C. As TLC showed completion of reaction, the solution was extracted with dichloromethane (50 ml×2). The combined organic layer was dried on Na$_2$SO$_4$ and evaporated under vacuum to provide white solid as a Step-4 product (1.95 gm) in 80% yield.

Analysis:
MS (ES−) $C_9H_{12}N_4O_6S.N(C_4H_9)_4$ as a salt=303.2 (M−1) as a free sulfonic acid;
H$^1$NMR (CDCl$_3$)=4.65 (d, 1H), 4.39 (br s, 1H), 3.23-3.31 (m, 8H), 2.84 (d, 1H), 2.54 (s, 3H), 2.21-2.34 (m, 3H), 1.98-2.01 (m, 1H), 1.49-1.70 (m, 8H), 1.29-1.49 (m, 8H), 0.95 (t, 12H).

Step-5: Sodium salt of trans-6-sulphooxy-2-(5-methyl-[1,3,4]-oxadiazol-2-yl)-7-oxo-1,6-diazabicyclo[3.2.1]-octane The compound (0.546 gm) obtained as a Step-4 product was loaded in tetrahydrofuran and water 1:9 mixture (10 ml) and passed slowly through freshly activated sodium form of Amberlite 200 C resin (50 gm). The fractions were analyzed on TLC and combined fractions were evaporated to remove lower boiling solvent under vacuum below 40° C. The aqueous layer was then washed with dichloromethane (10 ml×2) and layers were separated. The aqueous layer was concentrated under vacuum below 40° C. to provide residue which was triturated with acetone. The solid was obtained to provide Example-1 compound of the invention (0.3 gm) in 90% yield.
Analysis:
MS (ES−) $C_9H_{11}N_4O_6SNa$=303.3 (M−1) as a free sulfonic acid;
H$^1$NMR (DMSO-d$_6$)=4.59 (d, 1H), 4.04 (br s, 1H), 2.92 (br d, 1H), 2.73 (d, 1H), 2.5 (s, 3H), 2.10-2.16 (m, 1H), 1.92-2.02 (m, 2H), 1.80-1.88 (m, 1H).

Compounds 2 to 12 (Table 1) were prepared using the procedure described as in Example-1 and using corresponding R$_1$CONHNH$_2$, in the place of acetic acid hydrazide.

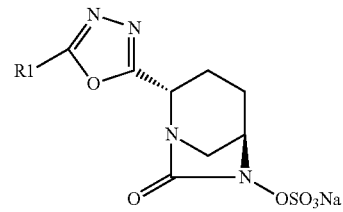

TABLE 1

| Example No. | Acid hydrazide (R$_1$CONHNH$_2$) | R$_1$ | H$^1$ NMR (DMSO-d$_6$) | Mass (ES-1) as free acid (MF) |
|---|---|---|---|---|
| 2. | C$_2$H$_5$—CONHNH$_2$ | —C$_2$H$_5$ | 4.59 (d, 1H), 4.03 (br s, 1H), 2.93 (br d, 1H), 2.84 (q, 2H), 2.59 (d, 1H), 2.06-2.16 (m, 1H), 1.94-2.02 (m, 2H), 1.83-1.88 (m, 1H), 1.25 (q, 3H). | 317.1 (C$_{10}$H$_{13}$N$_4$O$_6$S•Na) |
| 3. | CF$_3$—CONHNH$_2$ | —CF$_3$ | 4.73, (d, 1H), 4.06 (br s, 1H), 2.93 (br d, 1H), 3.00 (d, 1H), 2.12-2.25 (m, 1H), 1.95-2.02 (m, 2H), 1.80-1.90 (m, 1H). | 357.2 (C$_9$H$_8$F$_3$N$_4$O$_6$S•Na) |
| 4. | NH$_2$CO—CONHNH$_2$ | NH$_2$CO— | 8.62 (s, 1H), 8.20 (s, 1H), 4.70 (d, 1H), 4.05 (br s, 1H), 2.94 (br d, 1H), 2.79 (d, 1H), 2.18-2.24 (m, 1H), 1.98-2.10 (m, 2H), 1.81-1.90 (m, 1H). | 332.3 (C$_9$H$_{10}$N$_5$O$_7$S•Na) |

TABLE 1-continued

| Example No. | Acid hydrazide (R₁CONHNH₂) | R₁ | H¹ NMR (DMSO-d₆) | Mass (ES-1) as free acid (MF) |
|---|---|---|---|---|
| 5. | isoxazol-3-yl-CONHNH₂ | isoxazol-3-yl | 9.30 (d, 1H), 7.30 (d, 1H), 4.76 (d, 1H), 4.06 (br s, 1H), 2.98 (br d, 1H), 2.85 (d, 1H), 2.10-2.28 (m, 1H), 1.98-2.10 (m, 2H), 1.82-1.95 (m, 1H). | 356.2 ($C_{11}H_{10}N_5O_7S\cdot Na$) |
| 6. | furan-2-yl-CONHNH₂ | furan-2-yl | 8.05 (s, 1H), 7.40 (d, 1H), 6.78 (s, 1H), 4.70 (d, 1H), 4.05 (br s, 1H), 2.96 (br d, 1H), 2.81 (d, 1H), 2.19-2.30 (m, 1H), 1.80-2.10 (m, 2H), 1.84-1.95 (m, 1H). | 355.2 ($C_{12}H_{11}N_4O_7S\cdot Na$) |
| 7. | phenyl-CONHNH₂ | phenyl | 8.01 (d, 1H), 7.58-7.65 (m, 1H), 4.72 (d, 1H), 4.07 (br s, 1H), 2.98 (br d, 1H), 2.85 (d, 1H), 2.20-2.27 (m, 1H), 1.96-2.08 (m, 2H), 1.87-1.94 (m, 1H). | 365.2 ($C_{14}H_{13}N_4O_6S\cdot Na$) |
| 8. | pyridin-2-yl-CONHNH₂ | pyridin-2-yl | 8.78 (d, 1H), 8.19 (d, 1H), 8.031-8.07 (m, 1H), 7.62-7.65 (m, 1H), 4.76 (d, 1H), 4.07 (br s, 1H), 3.00 (br d, 1H), 2.83 (d, 1H), 2.20-2.30 (m, 1H), 2.00-2.11 (m, 2H), 1.87-1.94 (m, 1H). | 366.2 ($C_{13}H_{12}N_5O_6S\cdot Na$) |
| 9. | 6-(H₂NCO)-pyridin-2-yl-CONHNH₂ | 6-(H₂NCO)-pyridin-2-yl | 8.35-8.37 (m, 1H), 8.20-8.23 (m, 2H), 8.01 (br s, 1H), 7.85 (br s, 1H), 4.78 (d, 1H), 4.08 (br s, 1H), 3.99 (br d, 1H), 2.90 (d, 1H), 2.25-2.31 (m, 1H), 2.02-2.12 (m, 2H), 1.93-1.97 (m, 1H). | 409.2 ($C_9H_{11}N_4O_6S\cdot Na$) |
| 10. | 6,7-dihydro-5H-imidazo[2,1-c][1,4]oxazin-2-yl-CONHNH₂ | 6,7-dihydro-5H-imidazo[2,1-c][1,4]oxazin-2-yl | 8.03 (s, 1H), 4.78 (s, 2H), 4.68 (d, 1H), 4.10-4.12 (m, 2H), 4.01-4.05 (m, 3H), 2.97 (br d, 1H), 2.75 (d, 1H), 2.10-2.20 (m, 1H), 1.99-2.07 (m, 2H), 1.89-1.96 (m, 1H). | 411.2 ($C_{14}H_{15}N_6O_7S\cdot Na$) |
| 11. | morpholin-4-yl-CH₂-CONHNH₂ | morpholin-4-yl-CH₂- | 4.64 (d, 1H), 4.04 (br s, 1H), 3.76-3.86 (m, 2H), 3.56 (t, 4H), 2.94 (br d, 1H), 2.69 (d, 1H), 2.44-2.48 (m, 4H), 2.12-2.22 (m, 1H), 1.93-2.06 (m, 2H), 1.60-1.80 (m, 1H). | 388.2 ($C_{13}H_{18}N_5O_7S\cdot Na$) |
| 12. | morpholin-4-yl-CO-CONHNH₂ | morpholin-4-yl-CO- | 4.71 (d, 1H), 4.06 (br s, 1H), 3.92-3.96 (m, 2H), 3.60-3.69 (m, 6H), 2.98 (br d, 1H), 2.78 (d, 1H), 2.18-2.22 (m, 1H), 1.95-2.05 (m, 2H), 1.80-1.90 (m, 1H). | 402.0 ($C_{13}H_{16}N_5O_8S\cdot Na$) |

Example-13 trans-sulfuric acid mono-[2-(5-aminomethyl-[1,3,4]-oxadiazol-2-yl)-7-oxo-1,6-diazabicyclo[3.2.1]-octan-6-yl]ester

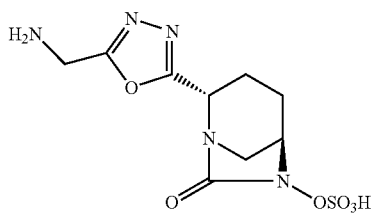

Tetrabutylammonium salt of trans-sulfuric acid mono-[2-(5-aminomethyl-[1,3,4]-oxadiazol-2-yl)-7-oxo-1,6-diazabicyclo[3.2.1]-octan-6-yl]ester (600 mg, obtained by following procedure from Step-1 to Step-4 as described in Example-1 and by using tert-butoxycarbonylamino acetic acid hydrazide in the place of acetic acid hydrazide) was added, a solution of trifluoroacetic acid (1.2 ml) in dichloromethane (1.2 ml) slowly by syringe at −5° C. over a period of 5 minutes. The mixture was maintained under stirring for 1 hour. Solvents were removed below 40° C. under high vacuum to provide a residue which was triturated with diethyl ether (50 ml×5) and each time diethyl ether was decanted. The obtained white solid was further triturated with acetonitrile (50 ml×2). The resultant solid was stirred in dichloromethane (50 ml) and the suspension was filtered. The solid was dried under vacuum to provide title compound of invention in 0.265 gm quantity.

Analysis:

MS (ES−) $C_9H_{13}N_5O_6S.CF_3COOH=318.2$ (M−1) as a free sulfonic acid;

$H^1$NMR (DMSO-$d_6$ after D2O exchange)=4.69 (d, 1H), 4.45 (s, 2H), 4.09 (br s, 1H), 2.97 (br d, 1H), 2.74 (d, 1H), 2.17-2.19 (m, 1H), 1.94-2.10 (m, 2H), 1.80-2.00 (m, 1H).

Compounds 14 to 19 (Table 2) were prepared using a procedure described in Example-13 and using corresponding $R_1CONHNH_2$, wherein the amine function is protected with BOC group.

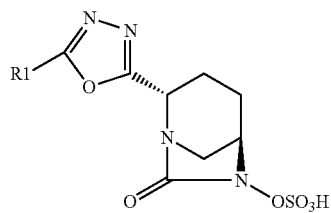

Example-20

Sodium salt of trans-6-(sulphooxy)-2-(5-methyl-[1,3,4]-thiadiazol-2-yl)-7-oxo-1,6-diazabicyclo[3.2.1]-octane

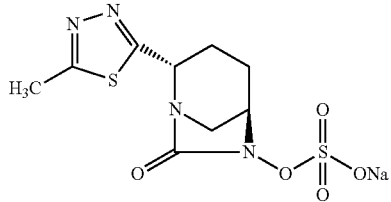

Step-1: Preparation of trans-2-(N''-acetylhydrazinocarbonyl)-5-benzyloxyamino-piperidine-1-carboxylic acid-tert-butyl ester To a solution of trans-5-benzyloxyamino-piperidine-1,2-dicarboxylic acid-1-tert-butyl ester (12 gm, 0.034 mol) in N,N-dimethyl formamide (60 ml), EDC-HCl (9.82 gm,

TABLE 2

| Example No. | Acid hydrazide ($R_1CONHNH_2$) | $R_1$ | $H^1$ NMR (DMSO-$d_6$) | Mass (ES-1) as free acid (MF) |
|---|---|---|---|---|
| 14. | Boc—NH—CH(CH₃)—CONHNH₂ | H₂N—CH(CH₃)— | 8.64, (br s, 3H), 4.87 (q, 1H), 4.69 (d, 1H), 4.09 (br s, 1H), 2.98 (br d, 1H), 2.75 (d, 1H), 2.16-2.21 (m, 1H), 2.00-2.21 (m, 2H), 1.82-1.90 (m, 1H), 1.58 (d, 3H). | 332.3 ($C_{10}H_{15}N_5O_6S$) |
| 15. | Boc—NH—CH(CH₃)—CONHNH₂ | H₂N—CH(CH₃)— | 8.65, (br s, 3H), 4.87 (q, 1H), 4.69 (d, 1H), 4.09 (br s, 1H), 2.98 (br d, 1H), 2.73 (d, 1H), 2.16-2.21 (m, 1H), 1.99-2.09 (m, 2H), 1.82-1.90 (m, 1H), 1.58 (d, 3H). | 332.2 ($C_{10}H_{15}N_5O_6S$) |
| 16. | boc-N(piperidine)-CONHNH₂ | HN(piperidine)- | 8.50 (br s, 1H), 8.32 (br s, 1H), 4.61 (d, 1H), 4.05 (br s, 1H), 3.26-3.29 (m, 2H), 3.04 (t, 2H), 2.93-3.02 (br d, 1H), 2.72 (d, 1H), 2.13-2.20 (m, 3H), 1.82-2.02 (m, 6H). | 372.2 ($C_{13}H_{18}N_5O_6S$) |
| 17. | pyrrolidine(boc)-CONHNH₂ | pyrrolidine(H)- | 9.48 (br s, 2H), 5.04 (t, 1H), 4.67 (d, 1H), 4.09 (br s, 1H), 3.30-3.39 (m, 2H), 2.98 (br d, 1H), 2.81 (d, 1H), 2.38-2.46 (m, 1H), 2.22-2.34 (m, 1H), 2.17-2.20 (m, 1H), 1.98-2.10 (m, 4H), 1.80-1.89 (m, 1H). | 358.3 ($C_{12}H_{17}N_5O_6S$) |
| 18. | boc-piperazine-CH₂-CONHNH₂ | HN-piperazine-CH₂- | 8.45 (br s, 2H), 4.63 (d, 1H), 4.06 (br s, 1H), 3.91-3.99 (m, 2H), 3.10 (br s, 4H), 2.96 (br d, 1H), 2.65-2.73 (m, 5H), 2.05-2.20 (m, 1H), 1.94-2.05 (m, 2H), 1.80-1.88 (m, 1H). | 387.2 ($C_{13}H_{20}N_6O_6S$) |
| 19. | Ph-CH(NHBoc)-CONHNH₂ | Ph-CH(NH₂)- | 9.31 (br s, 2H), 7.43-7.55 (m, 6H), 6.19 (s, 1H), 4.69 (dd, 1H), 4.07 (br s, 1H), 2.91-3.00 (m, 2H), 2.64-2.70 (m, 1H), 2.12-2.20 (m, 1H), 1.94-2.04 (m, 2H), 1.80-1.90 (m, 1H). | 393.9 ($C_{15}H_{17}N_5O_6S$) |

0.051 mol) and N-methyl morpholine (11.4 ml) were added successively at 10° C. to 15° C. under stirring. To the reaction mixture, were added acetyl hydrazide (2.79 gm, 0.0377 mol) and HOBt (4.62 gm, 0.034 mol). The resulting mixture was allowed to warm at 25° C. to 35° C. and stirred for 16 hours. The reaction mixture was poured into water (600 ml) and stirred for 30 min. The separated solid was filtered and the filtrate was extracted with ethyl acetate (3×400 ml). The combined organic extract was dried over sodium sulphate and the solvent was evaporated under vacuum to provide a residue. The residue was purified by column chromatography to obtain the Step-1 product, as a pale yellow thick oil in 9.8 gm quantity (yield 70%).

Analysis:

MS: 407 (M+H); MF: $C_{20}H_{30}N_4O_5$; MW: 406.49.

Step-2: Preparation of trans-2-(5-methyl-[1,3,4]-thiadiazol-2-yl)-5-benzyloxyamino-piperidine-1-carboxylic acid-tert-butyl ester To a solution of step-1 product (9.6 gm, 0.0236 mol) in toluene (240 ml) was added Lawesson's reagent (12.4 gm, 0.0307 mol) and the resulting mixture heated to 60° C. to 65° C. for 2 hours under stirring. The reaction mixture was allowed to cool to 25° C. to 35° C. and washed with saturated sodium bicarbonate solution (2×150 ml). The organic layer was separated, dried and the solvent was evaporated under vacuum to provide a residue. The residue was purified by column chromatography to obtain step-2 product as pale yellow oil, in 9.5 gm quantity.

Analysis:

MS: 405 (M+H); MF: $C_{20}H_{28}N_4O_3S$; MW: 404.54;

Step-3: Preparation of trans-2-(5-methyl-[1,3,4]-thiadiazol-2-yl)-5-benzyloxyamino-piperidine To a solution of Step-2 product (9.5 gm, 0.0236 mol) in dichloromethane (19 ml) was added trifluoro acetic acid (38 ml) at 10-15° C., over a period of 5 min, under stirring. The resulting solution was allowed to stir at 25° C. to 35° C. for 30 min and the solution was concentrated under vacuum to provide a residue. The residue was diluted with water (50 ml) and aqueous sodium bicarbonate solution. It was extracted with ethyl acetate (2×100 ml). The combined organic layer was dried over sodium sulphate and was evaporated under vacuum to provide a residue. The residue was purified by column chromatography to obtain step-3 product, as off-white solid, in 4.4 gm quantity (yield 62%)

Analysis:

MS: 305 (M+H); MF: $C_{15}H_{20}N_4OS$; MW: 305.

Step-4: Preparation of trans-2-(5-methyl-[1,3,4]-thiadiazol-2-yl)-6-benzyloxy-7-oxo-1,6-diazabicyclo[3.2.1]-octane To a solution of Step-3 product (4.4 gm, 0.0144 mol) and triethylamine (6.02 ml, 0.0432 mol) in acetonitrile (66 ml) was added a solution of triphosgene (2.57 gm, 0.00865 mol) in acetonitrile (22 ml) at 10° C. to 15° C. over a period of 10 minutes under stirring. N,N dimethylamino pyridine (176 mg, 0.00144 mol) was added to the reaction mixture after 30 min. and the mixture was then allowed to warm to 25° C. to 35° C. and stirred for 16 hours. The resulting mixture was quenched with saturated sodium bicarbonate solution (30 ml). The solvents were evaporated under vacuum to provide a residue. The residue was purified by column chromatography to obtain the Step-4 product as off-white solid in 1.1 gm quantity (yield 23%).

Analysis:

MS: 331 (M+H); MF: $C_{16}H_{18}N_4O_2S$; MW: 330.

Step-5: Preparation of trans-2-(5-methyl-[1,3,4]-thiadiazol-2-yl)-6-hydroxy-7-oxo-1,6-diazabicyclo[3.2.1]-octane To a solution of Step-4 product (1.1 gm, 0.0033 mol) in methanol (100 ml), was added ammonium formate (10 gm) followed by 10% Pd/C (2.2 gm, 2 times w/w). The suspension was stirred for 4 hrs at 25° C. to 35° C. The catalyst was filtered thorough celite, and the filtrate was concentrated under vacuum to obtain Step-5 product in 0.7 gm quantity (yield 90%), which was used as such for the next reaction.

Analysis:

MS: 241 (M+H); MF: $C_9H_{12}N_4O_2S$; MW: 240

Step-6: Preparation of tetrabutylammonium salt of trans-6-(sulphooxy)-2-(5-methyl-[1,3,4]-thiadiazol-2-yl)-7-oxo-1,6-diazabicyclo[3.2.1]-octane To a solution of Step-5 product (630 mg) in a mixture of N,N-dimethyl formamide: dichloromethane (3 ml: 3 ml) was added N,N-dimethyl formamide sulfur trioxide complex (480 mg) at 0° C. to 5° C. under stirring. The reaction mixture was stirred for 30 min. It was concentrated under vacuum to remove dichloromethane and to the leftover solution, was added a solution of tetrabutyl ammonium acetate (956 mg) in water (3 ml). The reaction mixture was stirred for 16 hours at 25° C. to 35° C. It was concentrated under reduced pressure (4 mm Hg) to provide a residue. To the residue, water (10 ml) was added and the mixture was extracted with dichloromethane (2×15 ml). The combined organic layer was concentrated under vacuum to obtain the step-6 product as a white solid in 590 mg quantity (yield 54%).

Analysis:

MS: 562 (M+H); MF: $C_{25}H_{47}N_5O_5S_2$; MW: 561

Step-7: Sodium salt of trans-6-(sulphooxy)-2-(5-methyl-[1,3,4]-thiadiazol-2-yl)-7-oxo-1,6-diazabicyclo[3.2.1]-octane The product obtained as in Step-6 was dissolved in 20% tetrahydrofuran in water (1 ml) and the above solution was passed through a column of Amberlite SR01-L-Na resin (15 g). The column was first eluted with THF-water (10:1, 50 ml) followed by water (50 ml). The combined aqueous layer fractions were evaporated under vacuum to obtain the compound of invention as off-white solid in 250 mg quantity (Yield 70%).

Analysis:

MS: 319 (M–H of free sulphonic acid); MF: $C_9H_{11}N_4O_5S_2Na$; MW: 342.33

$H^1$NMR ($D_2O$)=4.85 (d, 1H), 4.122 (br s, 1H), 3.11 (br d, 1H), 2.88 (d, 1H), 2.66 (s, 3H), 2.42-2.37 (m, 1H), 2.16-2.05 (m, 2H), 1.89-1.82 (m, 1H).

Example-21

Sodium salt of trans-6-(sulphooxy)-2-(5-methyl-[1,2,4]-oxadiazol-3-yl)-7-oxo-1,6-diazabicyclo[3.2.1]-octane

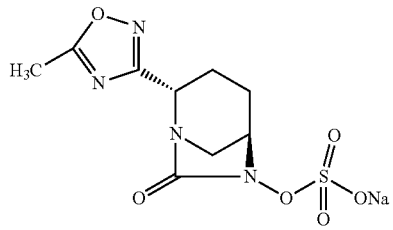

Step-1: Preparation of trans-5-benzyloxyamino-2-carboxamido-piperidine-1-carboxylic acid-1-tert-butyl ester To a stirred solution of trans-5-benzyloxyamino-piperidine-1,2-dicarboxylic acid-1-tert-butyl ester (21 gm, 0.06 moles) and triethylamine (25.12 ml, 0.18 moles) in dichloromethane (210 ml) was added pivaloyl chloride (11.07 ml, 0.09 moles) dropwise at a temperature of 0° C. The resulting mixture was stirred for 1.5 hours. The reaction mixture was cooled to −40° C. and dry ammonia gas was bubbled for 30 min. It was allowed to warm to 25° C. to 35° C. and the resulting suspension was filtered off. The filtrate was evaporated under reduced pressure to provide a residue, and the residue was chromatographed on a column of silica gel to provide the step-1 product, as thick oil, in 10.2 gm quantity, (yield: 49%).
Analysis:
MS: 348 [M+]; MF: $C_{19}H_{28}N_2O_4$; MW: 348.

Step-2: Preparation of trans-5-benzyloxyamino-2-cyano-piperidine-1-carboxylic acid-1-tert-butyl ester To a solution of Step-1 compound (10.2 gm, 0.0286 moles) and triethylamine (17.99 ml, 1.289 moles) in dichloromethane (306 ml) was added of trifluoro acetic anhydride (12.08 gm, 0.0573 moles) at 0° C. under stirring. The resulting solution was allowed to warm to 25° C. to 35° C. and stirred for 6 hours. The reaction mixture was washed successively by water (3×100 ml), saturated aqueous ammonium chloride solution (100 ml) and brine (100 ml). The combined organic layer was dried over sodium sulfate and the solvent was evaporated under vacuum to provide a residue. The residue was chromatographed on a column of silica gel using a mixture of acetone:hexane (1:19), to provide the step-2 product, as a white solid, in 9.7 gm quantity (yield—quantitative).
Analysis:
MS: 331 (M+); MF: $C_{18}H_{25}N_3O_3$; MW: 331.

Step-3: Preparation of trans-5-benzyloxyamino-2-(N-hydroxy-carbamimidioyl)-piperidine-1-carboxylic acid-1-tert-butyl ester To a cooled solution of step-2 product (9.7 gm, 0.0293 moles) in methanol (145.5 ml) was added successively, hydroxylamine hydrochloride (3.05 gm, 0.0439 moles) and sodium bicarbonate (5.53 gm, 0.0659 moles) at 0° C. under stirring. The reaction mixture was allowed to warm to 25° C. to 35° C. and stirred for 24 hrs. The resulting suspension was filtered off and the filtrate was concentrated under vacuum below 40° C. to provide a residue. The residue was purified by column chromatography over silica-gel with a mixture of acetone:hexane (1:5) to provide the step-3 product, as colorless oil, in 7.6 gm quantity (yield: 72%).
Analysis:
MS: 364 (M+); MF: $C_{18}H_{28}N_4O_4$; MW: 364.

Step-4: Preparation of trans-5-benzyloxyamino-2-(N-acetyloxy-carbamimidioyl)-piperidine-1-carboxylic acid-1-tert-butyl ester To a solution of Step-3 product (7.6 gm, 0.0208 moles) in dichloromethane (76 ml) was added triethylamine (5.82 ml, 0.0417 moles) followed by acetic anhydride (2.34 gm, 0.02293 moles) dropwise at 0° C. The resulting mixture was allowed to warm to 25° C. to 35° C. and stirred for 4 hours. The reaction mixture was washed successively, with water (2×75 ml), saturated aqueous ammonium chloride solution (75 ml), and brine (35 ml). The organic layer was dried over sodium sulfate and evaporated under vacuum to provide a residue. The residue was chromatographed on a column of silica gel with 1:10 mixture of acetone: hexane to yield Step-4 product as white solid, in 7.5 gm quantity (yield: 88%).
Analysis:
MS: 405 (M+); MF: $C_{21}H_{31}N_3O_5$; MW: 405.

Step-5: Preparation of trans-5-benzyloxyamino-2-(5-methyl-[1,2,4]-oxadiazol-3-yl)-piperidine-1-carboxylic acid-1-tert-butyl ester A solution of Step-4 product (7.5 gm) in pyridine (112.5 ml) was heated at reflux temperature for 6 hours. The solvent was evaporated under vacuum below 40° C., and the residue was diluted with 10% aqueous $KHSO_4$ solution (100 ml). The mixture was extracted with ethyl acetate (3×75 ml). The combined organic extracts were washed with water (2×75 ml) followed by brine (37.5 ml). Organic layer was dried over sodium sulfate and the solvent was evaporated under vacuum to provide a residue. The residue was purified by column chromatography with 1:20 mixture of acetone: hexane, to afford the step-5 product as a white solid, in 6.0 gm quantity (yield: 84)%.
Analysis:
MS: 387 (M+); MF: $C_{21}H_{29}N_3O_4$; MW: 387.

Step-6: Preparation of trans-6-benzyloxyamino-2-(5-methyl-[1,2,4]-oxadiazol-3-yl)-7-oxo-1,6-diazabicyclo[3.2.1]-octane To a solution of Step-5 product (6 gm) in dichloromethane (150 ml) was added trifluoro acetic acid (12 ml) at −15° C. under stirring and the resulting mixture was allowed to warm to 25° C. to 35° C. It was stirred for 4 hours. The solvent was evaporated under vacuum below 40° C. The resulting mass was diluted with saturated aqueous sodium bicarbonate solution (60 ml) and the mixture was extracted with dichloromethane (2×60 ml). The combined organic extracts were washed with water (60 ml), dried over sodium sulphate and evaporated under vacuum below 40° C. to obtain 4.2 gm of tert-butoxycarbonyl group deprotected piperidine compound.
To the solution of tert-butoxycarbonyl group deprotected piperidine compound (4.2 gm) in acetonitrile (63 ml) was added triethyl amine (5.28 ml) followed by a solution of triphosgene (1.9 gm) in acetonitrile (16.8 ml) at 0° C. to 5° C. under stirring. It was stirred for 30 min and N,N-dimethyl amino pyridine (0.178 gm) was added. The reaction mixture was allowed to warm to 25° C. to 35° C. and stirred for 16 hours. To the reaction mixture saturated aqueous solution of sodium bicarbonate (33.6 ml) was added and the resulting mixture was stirred for 30 min. The mixture was concentrated to its ⅓$^{rd}$ volume under vacuum and it was diluted with water (42 ml) and the resulting mixture extracted with dichloromethane (2×40 ml). The combined organic layer was evaporated under vacuum to provide a residue and the residue purified over a column of silica gel using 1:4 mixture of acetone: hexane to provide the step-6 product as white solid, in 2.3 g quantity (yield: 48%).

Analysis:
MS: 314 (M+); MF; $C_{16}H_{18}N_4O_3$; MW; 314.

Step-7: Preparation of tetrabutylamoonium salt of trans-6-sulfooxy-2-(5-methyl-[1,2,4]-oxadiazol-3-yl)-7-oxo-1,6-diaza-bicyclo[3.2.1]-octane A solution of Step-6 product (2.3 gm, 0.00732 mole) in a mixture of dichloromethane and N,N-dimethylformamide (11.5 ml each) was added 10% palladium on carbon (575 mg) and the suspension was stirred under hydrogen atmosphere (1 atm) at 25° C. to 35° C. for 5 hours. The catalyst was filtered and the filtrate was concentrated under reduced pressure to obtain the debenzylated product. This was used as such for the next reaction. The debenzylated product obtained as above, was dissolved in N,N-dimethylformamide (11.5 ml), and to the clear solution was added in one portion N,N-dimethyl formamide sulfur trioxide complex (1.34 gm, 0.00878 mole) under argon atmosphere, at 0° C. The reaction mixture was stirred for 1 hour. Tetra butyl ammonium sulfate (2.66 gm, 0.0.00878 mole) dissolved in water (8.8 ml) was added to the reaction mixture and the resulting mixture was allowed to warm to 25° C. to 35° C. and stirred for 1 hour. The solvents were removed under vacuum below 40° C. to provide a residue and it was triturated with xylene (25 ml) to remove traces of N,N'-dimethylformamide. The residue was partitioned between a 1:1 mixture of water (23 ml) and dichloromethane (23 ml) and layers were separated. The aqueous layer was re-extracted with dichloromethane (23 ml). The combined organic extracts were washed successively with water (23 ml) and brine (23 ml). The organic layer was dried over sodium sulfate and concentrated under vacuum to obtain the step-7 product in 2.05 gm quantity (yield—51%).

Analysis:
MS: 304 (M–H) of sulfate; M.F: $C_{25}H_{47}N_5O_6S$; M.W: 545.7.

Step-8: Sodium salt of trans-6-sulfooxy-2-(5-methyl-[1,2,4]-oxadiazol-3-yl)-7-oxo-1,6-diaza-bicyclo[3.2.1]-octane The Step-7 product (1.7 g) was dissolved in 5% tetrahydrofuran in water mixture (2 ml), and the solution was loaded on a column of Dowex 50WX8 200 Na$^+$ resin (25 cm×3.0 cms). The column was eluted with 5% tetrahydrofuran in water (50 ml) followed by water (150 ml). Evaporation of the fractions under vacuum below 40° C. provided the title compound of the invention, as a white solid, in 860 mg quantity (yield 85%).

Analysis:
MS: 304 (M–H) of sulfate; M.F: $C_9H_{11}N_4NaO_6S$; M.W: 326.27.
H$^1$NMR (DMSO-d$_6$ after D$_2$O exchange)=4.46 (t, 1H), 4.02 (br s, 1H), 2.90 (br s, 2H), 2.59 (s, 3H), 2.06-1.93 (m, 3H), 1.83-1.77 (m, 1H).

Example-22

Sodium salt of trans-6-(sulphooxy)-2-(5-ethoxycarbonyl-[1,2,4]-oxadiazol-3-yl)-7-oxo-1,6-diazabicyclo[3.2.1]-octane

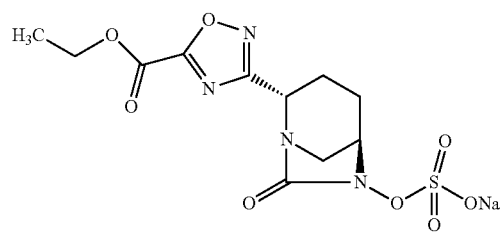

By following the procedure described in Example-21 and using ethyl ester of oxalyl chloride in the place of acetic anhydride in Step-4, the title compound was obtained in 731 mg quantity.

Analysis:
MS: 333 (M–H) of sulfate; M.F: $C_9H_{10}N_5NaO_7S$; M.W: 355.
H$^1$NMR (DMSO-d$_6$ after D$_2$O exchange)=4.61 (d, 1H), 4.41 (q, 2H), 4.04 (br s, 1H), 2.92-2.82 (m, 2H), 2.09-2.03 (m, 2H), 1.99-1.96 (m, 1H), 1.83-1.81 (m, 1H), 1.33 (t, 3H).

Example-23

Sodium salt of trans-6-(sulphooxy)-2-(2-methyl-2H-[1,2,3,4]-tetrazol-5-yl)-7-oxo-1,6-diazabicyclo[3.2.1]-octane

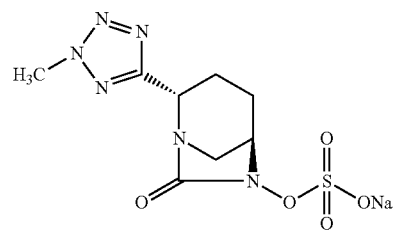

Step-1: Preparation of trans-5-benzyloxyamino-2-(1H-tetrazol-5-yl)-piperidine-1-carboxylic acid-1-tert-butyl ester To a solution of trans-5-benzyloxyamino-2-cyano-piperidine-1-carboxylic acid-1-tert-butyl ester (6 gm, 0.018 mol) in toluene (120 ml) were added sodium azide (5.88 gm, 0.090 mol), triethylamine hydrochloride (12.42 gm, 0.090 mol) and the resulting mixture was heated to 100° C., under stirring for 2 hours. The reaction mixture was cooled to 25° C. to 35° C. and poured into saturated aqueous ammonium chloride solution (150 ml). The mixture was stirred for 15 min and aqueous layer was extracted with ethyl acetate (1×120 ml). The combined organic layer was dried over sodium sulfate and was concentrated under vacuum to obtain the step-1 product as colorless oil, in 6.0 gm quantity (yield 89%).
Analysis:
MS: 375 (M−H); FW: $C_{18}H_{26}N_6O_3$; MW: 376.

Step-2: Preparation of isomers: isomer A trans-5-benzyloxyamino-2-(1-methyl-1H-tetrazol-5-yl)-piperidine-1-carboxylic acid-1-tert-butyl ester and isomer B trans-5-benzyloxyamino-2-(2-methyl-2H-tetrazol-5-yl)-piperidine-1-carboxylic acid-1-tert-butyl ester To a mixture of step-1 product (6.0 gm, 0.0168 mol) and cesium carbonate (7.84 gm, 0.0240 mol) in N,N-dimethylformaide (60 ml) was added methyl iodide (3.41 gm, 0.0240 mol) at a temperature of 0° C. to 5° C., under stirring. The reaction mixture was stirred for 30 min, warmed to 25° C. to 35° C. and stirred for 2 hours. It was poured onto ice water (600 ml) and extracted with ethyl acetate (3×150 ml). The combined organic layer was dried over sodium sulfate and concentrated under vacuum to provide a residue. The residue was purified by column chromatography using mixtures of 5-20% ethyl acetate in hexane to obtain two isomers Isomer A at Rf 0.50 and Isomer B: at Rf 0.42. These isomers were individually identified. Total quantity of products obtained was 5.7 gm (yield 91%).
Analysis:
MS: 389 (M−H); FW: $C_{19}H_{28}N_6O_3$; MW: 390

Step-3: Preparation of trans-5-benzyloxyamino-2-(2-methyl-2H-tetrazol-5-yl)-piperidine-1-carboxylic acid To a solution of isomer B as obtained in Step-2 (1.35 gm, 0.00347 mol) in dichloromethane (13.5 ml) was added trifluoro acetic acid (2.7 ml) at 0° C., under stirring. It was allowed to warm to 25° C. to 35° C. and stirred for 4 hours. The reaction mixture was concentrated under vacuum to provide a residue and the residue was diluted with water (20 ml) and treated with saturated aqueous sodium bicarbonate solution (5 ml). The resulting mixture was extracted with dichloromethane (2×20 ml). The combined extracts were dried over sodium sulfate and concentrated under vacuum to obtain the step-3 product as colorless oil, in 900 mg quantity (yield 90%).
Analysis:
MS: 288 (M+); FW: $C_{14}H_{20}N_6O$; MW: 288.

Step-4: Preparation of trans-6-(benzyloxy)-2-(2-methyl-2H-[1,2,3,4]-tetrazol-5-yl)-7-oxo-1,6-diazabicyclo[3.2.1]-octane To a solution of Step-3 product (900 mg, 0.00321 mol) and triethylamine (1.3 ml, 0.00937 mol) in acetonitrile (13.5 ml) was added a solution of triphosgene (400 mg, 0.00137 mol) in acetonitrile (3.6 ml) at 0° C. under stirring. To the mixture was added N,N-dimethylamino pyridine (38 mg, 0.00031 mol) after 30 minutes and the reaction mixture was allowed to warm to 25° C. to 35° C. It was stirred for 16 hours. The reaction mixture was diluted with saturated aqueous sodium bicarbonate solution (9 ml) and the organic solvent was evaporated under reduced pressure to provide a mass. The mass was extracted with dichloromethane (2×10 ml). The combined organic layer was concentrated under vacuum to provide a residue and the residue was purified by column chromatography using mixtures of 15-20% ethyl acetate in hexane to provide the Step-4 product as colorless oil, in 300 mg quantity (yield 32%).
Analysis:
MS: 315 (M+H): FW: $C_{15}H_{18}N_6O_2$; MW: 314.35.

Step-5: Preparation of trans-6-(hydroxy)-2-(2-methyl-2H-[1,2,3,4]-tetrazol-5-yl)-7-oxo-1,6-diazabicyclo[3.2.1]-octane To a solution of Step-4 product (300 mg, 0.00095 mol) in a mixture of ethyl acetate: methanol (3 ml: 0.6 ml), was added 10% Pd/C (60 mg, 2 times w/w) and the mixture stirred under hydrogen atmosphere at 25° C. to 35° C. for 2 hours. The catalyst was filtered thorough celite and the filtrate was evaporated under vacuum to obtain the Step-5 product as colorless oil, in 200 mg quantity (yield 93%). This was used as such for the next reaction.
Analysis:
MS: 224 (M+); FW: $C_8H_{12}N_6O_2$; MW: 224.

Step-6: Preparation of tetrabutylammonium salt of trans-6-(sulphooxy)-2-(2-methyl-2H-[1,2,3,4]-tetrazol-5-yl)-7-oxo-1,6-diazabicyclo[3.2.1]-octane To a solution of Step-5 product (200 mg) in N,N-dimethyl formamide (1 ml) was added N,N-dimethyl formamide sulfur trioxide complex (488 mg) in one lot at 0° C. under stirring. The resulting mixture was allowed to warm at 25° C. to 35° C. and stirred for 2 hours. A solution of tetrabutylammonium acetate (636 mg) in water (2.1 ml) was added to the reaction mixture. The mixture was stirred further for 16 hours. The solvent was evaporated under vacuum below 40° C. temperature to provide a residue, and the residue was diluted with water (10 ml). The resulting mixture was extracted with dichloromethane (2×10 ml). The combined organic layer was concentrated under vacuum to obtain the Step-6 product as white solid, in 275 mg quantity (yield 51%).
Analysis:
MS: 599 (M+H); FW: $C_{25}H_{49}N_7O_5S$; MW: 599.

Step-7: Sodium salt of trans-6-(sulphooxy)-2-(2-methyl-2H-[1,2,3,4]-tetrazol-5-yl)-7-oxo-1,6-diazabicyclo[3.2.1]-octane The Step-6 product (270 mg) was dissolved in 20% tetrahydrofuran in water (2 ml) and the resulting solution was loaded on activated Dowex 50 WX8-200-Na column (45 cm length×3 cm diameter). The column was eluted with tetrahydrofuran (100 ml) followed by 50% tetrahydrofuran water mixture. The product containing fractions were evaporated under vacuum below 40° C. to obtain the title compound of invention, as a white hygroscopic solid, in 100 mg quantity (yield 67%).
Analysis:
MS: 303 (M−H as a free sulphonic acid); FW for $C_8H_{11}N_6NaO_5S$; MW: 326.27.
H$^1$NMR (DMSO-$d_6$ after $D_2O$ exchange)=4.64 (t, 1H), 4.36 (s, 3H), 4.03 (br s, 3H), 2.85 (br s, 2H), 2.07-2.04 (m, 2H), 2.00 (m, 1H), 1.91-1.85 (m, 1H).

Example-24

Sodium salt of trans-6-(sulphooxy)-2-(1-methyl-1H-[1,2,3,4]-tetrazol-5-yl)-7-oxo-1,6-diazabicyclo[3.2.1]-octane

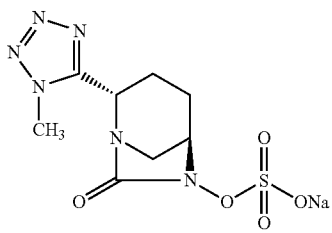

The title compound of invention was prepared by using isomer A obtained in Step-2 of Example-23 and by using the procedure described in Example-23 and using isomer obtained in Step-3.

Analysis:
H¹NMR (DMSO-d$_6$ after D$_2$O exchange)=4.82 (d, 1H), 4.04 (s, 3H), 2.83 (br d, 1H), 2.50 (d, 1H), 2.22-2.18 (m, 1H), 2.08-2.03 (m, 1H), 2.00-1.96 (m, 2H).

Example-25

Sodium salt of trans-6-sulphooxy-2-(3-ethoxycarbonyl-[1,2,4]-oxadiazol-5-yl)-7-oxo-1,6-diazabicyclo[3.2.1]-octane

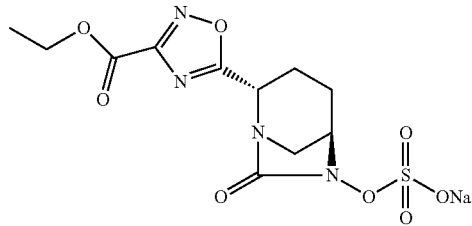

Step-1: Preparation of trans-6-benzyloxy-2-(ethoxycarbonylformamindino-N-oxy-carbonyl)-7-oxo-1,6-diazabicyclo[3.2.1]-octane To a solution of trans-6-benzyloxy-7-oxo-1,6-diazabicyclo[3.2.1]-octane-2-carboxylic acid (2.5 gm, 9.05 mmol) in N,N-dimethylformamide (25 ml) was added EDC hydrochloride (2.56 g, 13.58 mmol), HOBt (1.22 g, 9.05 mmol), N-hydroxy-ethoxycarbonylformamidine (669 mg, 9.05 mmol) and N-methyl morpholine (3 ml, 27.15 mmol) successively at a temperature between 10° C. to 15° C., under stirring. The reaction mixture was allowed to warm at 25° C. to 35° C. temperature and stirred for 24 hours. It was poured into water (250 mL) to provide a suspension. The suspension was filtered and the filtrate was extracted with ethyl acetate (3×100 mL). The combined organic extracts were dried over sodium sulfate and evaporated under vacuum to provide a residue. The residue was purified by column chromatography, using ethyl acetate, hexane (5:5) to obtain the Step-1 product, as a white solid, in 1.5 gm quantity (yield 42%) .eb;normal Analysis:
MS: 391 (M+H); MW: 390; M.F: C$_{18}$H$_{22}$N$_4$O$_6$

Step-2: Preparation of trans-6-benzyloxy-2-(3-ethoxycarbonyl-[1,2,4]-oxadiazol-5-yl)-7-oxo-1,6-diazabicyclo[3.2.1]-octane A solution of Step-1 product (1.5 gm) in pyridine (15 ml) was heated to 110° C. to 115° C. under argon atmosphere for 2.5 hours. The solvent was evaporated under vacuum to provide a residue. The residue was purified by column chromatography, using ethyl acetate, hexane (5:5) to provide step-2 product, as white solid, in 1 gm quantity (yield 70%).

Analysis:
MS: 373.2 (M+H); M.W: 372; M.F.: C$_{18}$H$_{20}$N$_4$O$_5$.

Step-3: Preparation of tetrabutylammonium salt of trans-6-sulphooxy-2-(3-ethoxycarbonyl-[1,2,4]-oxadiazol-5-yl)-7-oxo-1,6-diazabicyclo[3.2.1]-octane To a solution of Step-2 product (100 mg, 0.268 mmol) in a mixture of dichloromethane and N,N'-dimethylformamide (250 µL each) was added 10% palladium on carbon (25 mg) and the resulting mixture was stirred under hydrogen atmosphere for 1 hour at 25° C. to 35° C. The catalyst was filtered through micron filter and the filtrate was concentrated under vacuum below 40° C. to provide a residue. The residue was dissolved in N,N-dimethylformamide (500 µL) and N,N-dimethylformamide sulfurtrioxide complex (50 mg, 0.321 mmol) was added in one lot at 0° C. temperature. The mixture was stirred for 1 hour. The aqueous tetrabutyl ammonium acetate solution (97 mg, 0.321 mmol dissolved in 350 µL water) was then added to it. The reaction mixture was allowed to warm to 25° C. to 35° C. and stirred further for 1 hour. The volatiles were removed under vacuum to provide a residue and residue was triturated with xylene (10 ml) to remove traces of N,N-dimethylformamide. Residue was partitioned between water (10 ml) and dichloromethane (10 ml). Aqueous layer was re-extracted with dichloromethane (10 ml). Combined organic extracts were washed with water (10 ml) and brine (10 ml). Organic layer was dried over sodium sulfate and concentrated under vacuum to obtain yellow oil as the Step-3 product, in 100 mg quantity (yield 62%).

Analysis:
MS: 361.2 (M–H) of free sulfonic acid; M.W: 603: M.F: C$_{11}$H$_{13}$N$_4$O$_8$S:C$_{16}$H$_{36}$N.

Step-4: Sodium salt of trans-6-sulphooxy-2-(3-ethoxycarbonyl-[1,2,4]-oxadiazol-5-yl)-7-oxo-1,6-diazabicyclo[3.2.1]-octane The Step-3 product (100 mg) was dissolved in 50% aqueous tetrahydrofuran and the solution was loaded over Amberlite 200 Na⁺ resin column (20 cm length, 3 cm diameter). The column was eluted with 50% aqueous tetrahydrofuran. The desired fractions were evaporated under vacuum below 40° C. to provide title compound of the innovation as a white solid, in 30 mg quantity (yield 47%).

Analysis:
MP: 184-189 (Dec);
MS: 361.2 (M–H) as a free sulfonic acid; M.F: C$_{11}$H$_{13}$N$_4$O$_8$S Na.
H¹NMR (DMSO-d$_6$ after D$_2$O exchange)=4.81 (d, 1H), 4.42 (q, 2H), 4.03 (br s, 1H), 3.02 (br d, 1H), 2.79 (d, 1H), 2.22-2.16 (m, 1H), 2.09-1.96 (m, 2H), 1.85-1.82 (m, 1H), 1.32 (t, 3H).

Example-26 trans-6-(sulphooxy)-2-(5-(piperidin-4-yl-)-[1,2,4]-oxadiazol-3-yl)-7-oxo-1,6-diazabicyclo[3.2.1]-octane

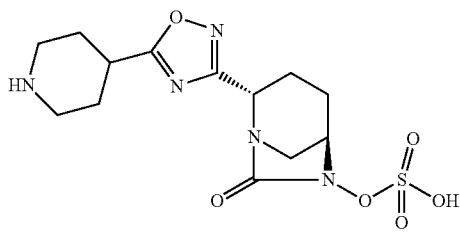 [SMILES: O=C1N2C[C@@H](CC[C@H]2c2noc(C3CCNCC3)n2)N1OS(=O)(=O)O]

By following the procedure described in Example-21 and using piperidine-4-carboxylic acid chloride in the place of acetic anhydride in Step-4, the title compound was obtained in 52 mg quantity.

Analysis:

MS: 373.1 (M–H) of sulfate; M.F: $C_{13}H_{19}N_5O_6S$;

$^1$H NMR (DMSO-d6): 8.52 (br s, 1H), 8.29 (br s, 1H), 4.50 (dd, 1H), 4.04 (dd, 1H), 3.47-3.30 (m, 1H), 3.05-3.034 (m, 3H), 2.94-2.86 (m, 3H), 2.22-2.19 (m, 2H), 2.03-1.81 (m, 6H).

Example-27

Sodium Salt of trans-6-(sulphooxy)-2-(5-carbox-amido-[1,2,4]-oxadiazol-3-yl)-7-oxo-1,6-diazabicyclo[3.2.1]-octane

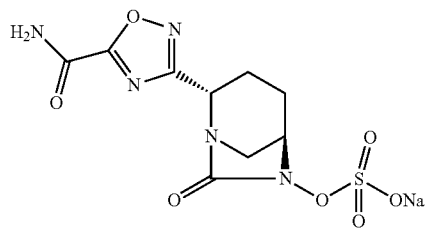

By following the procedure described in Example-21 and using carbamoyl chloride in the place of acetic anhydride in Step-4, the title compound was obtained in 102 mg quantity.

Analysis

MS: 332 (M–H); MF $C_9H_{11}N_5O_7SNa$; MW 333.28

$^1$H NMR (DMSO-d6): 8.766 (s, 1H), 8.359 (s, 1H), 4.59 (d, 1H), 4.03 (s, 1H), 2.91 (m, 2H), 2.0-2.48 (m, 3H), 1.85 (m, 1H).

Example-28

Sodium Salt of trans-6-(sulphooxy)-2-(5-(R)-piperidin-3-yl-[1,3,4]-oxadiazol-2-yl)-7-oxo-1,6-diazabicyclo[3.2.1]-octane

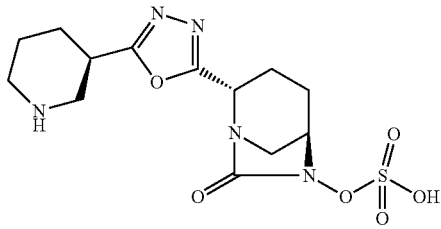 [SMILES: O=C1N2C[C@@H](CC[C@H]2c2nnc([C@@H]3CCCNC3)o2)N1OS(=O)(=O)O]

By following the procedure described in example-13 and using (R)—N-tert-butoxycarbonyl piperidine-3-carboxylic acid hydrazide in the place of tert-butoxycarbonylamino acetic acid hydrazide, the title compound was obtained in 35 mg quantity.

Analysis:

MS: 372.1 (M–H); MF $C_{13}H_{19}N_5O_6S$; MW 373.38

$^1$H NMR (DMSO-d6): 8.70 (s, 1H), 8.54 (s, 1H), 4.59 (dd, 1H), 4.06 (br s, 1H), 3.58 (br dd, 1H), 3.15-3.24 (m, 4H), 2.91-3.05 (m, 1H), 2.0-2.14 (m, 4H), 1.70-1.90 (m, 5H).

Compounds of the invention described in Example 1 to 28 were prepared using (S)-pyrroglutamic acid as a starting compound. The absolute stereochemistry is therefore (2S, 5R) 7-oxo-1,6-diaza-bicyclo[3.2.1]octane ring. Thus, the compound of Example-4, Sodium salt of trans-6-(sulphooxy)-2-(5-carboxamido-[1,3,4]-oxadiazol-2-yl)-7-oxo-1,6-diazabicyclo[3.2.1]-octane has the absolute stereochemistry as Sodium salt of (2S,5R)-6-(sulphooxy)-2-(5-carboxamido-[1,3,4]-oxadiazol-2-yl)-7-oxo-1,6-diazabicyclo[3.2.1]-octane. Alternatively, if the starting compound used is (R)-pyrroglutamic acid the resulting compounds will have (2R,5S) stereochemistry in 7-oxo-1,6-diaza-bicyclo[3.2.1]octane ring. A reference to a compound according to the invention also includes corresponding compounds having (2S,5R) (and 2R,5S) stereochemistry.

Biological Activity

The biological activity of representative compounds according to the invention against various bacterial strains was investigated. In a typical study, overnight grown bacterial cultures were diluted appropriately and inoculated on the agar media containing doubling dilutions of the test compounds. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), Performance Standards for Antimicrobial Susceptibility Testing, 20th Informational Supplement, M 100-S20, Volume 30, No. 1, 2010). The results of these studies are summarized in Tables 3 and 4. In general, the stand alone activity of compounds of invention was found to be >32 mcg/ml.

The antibacterial activity of representative compounds according to the invention was also investigated in combination with at least one antibacterial agent using the above study protocol and the results are given Table 3 and 4. As can be seen, the use of compounds according to the invention significantly lowered MIC values of the antibacterial agent (e.g. in this case Ceftazidime). The results also suggest the compounds according the invention increase antibacterial effectiveness of the antibacterial agent when said antibacterial agent is co-administered with a pharmaceutically effective amount of a compound of Formula (I) or a stereoisomer or a pharmaceutically acceptable salt thereof.

TABLE 3

Comparative activity of Ceftazidime (expressed as MIC in mcg/ml) in presence of representative compounds of the invention (each representative compound is present in a concentration of 4 mcg/ml)

| Compound of Example No. | E. coli NCTC 13351 | E. coli M50 | E. coli 7MP |
|---|---|---|---|
| 1 | 0.5 | 1 | 4 |
| 2 | 16 | 16 | 32 |
| 3 | 16 | 16 | 32 |
| 4 | 0.5 | 1 | 2 |
| 5 | 4 | 4 | 16 |
| 6 | 32 | 16 | 32 |
| 7 | 16 | 16 | 32 |
| 8 | 16 | 16 | 32 |
| 9 | 2 | 8 | >32 |
| 10 | 16 | 16 | 32 |
| 11 | 1 | 2 | 32 |
| 12 | 2 | 8 | 16 |
| 13 | 0.5 | 2 | 8 |
| 14 | 0.5 | 1 | 4 |
| 15 | 0.5 | 1 | 8 |
| 16 | 1 | 2 | 4 |
| 17 | 1 | 1 | 4 |
| 18 | 1 | 1 | 4 |
| 19 | 1 | 4 | 16 |
| 20 | 0.5 | 2 | 8 |
| 21 | 1 | 2 | 8 |
| 22 | 4 | 4 | 16 |
| 23 | 1 | 2 | 8 |
| 24 | 8 | 8 | 16 |
| 25 | 8 | 8 | 16 |
| 26 | 1 | 1 | 8 |
| 27 | 0.5 | 2 | 8 |
| 28 | >32 | >32 | >32 |

The invention claimed is:

1. A pharmaceutical composition comprising: (a) at least one antibacterial agent or a pharmaceutically acceptable derivative thereof; and (b) a compound of Formula (I)

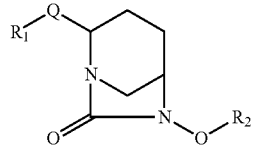

Formula (I)

or a stereoisomer or a pharmaceutically acceptable salt thereof, wherein:
Q is a heteroaryl selected from oxadiazole, thiadiazole and tetrazole;
$R_1$ is:
 (a) hydrogen,
 (b) $(CO)_n$—$R_3$, or
 (c) $COOR_4$,
n is 0 or 1;
$R_2$ is:
 (a) $SO_3M$
M is hydrogen or a cation;
$R_3$ is:
 (a) hydrogen,
 (b) $C_1$-$C_6$ alkyl optionally substituted with one or more substituents independently selected from halogen, $OR_5$, CN, $COOR_5$, $CONR_5R_7$, $NR_6R_7$, $NR_5COR_8$, $NR_5CONR_6R_7$, heterocyclyl, heteroaryl, cycloalkyl and aryl,
 (c) $NR_6R_7$,
 (d) $CONR_6R_7$,
 (e) aryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, and $NHCONR_6R_7$,

TABLE 4

Comparative activity of Ceftazidime (expressed as MIC in mcg/ml) in presence of representative compounds of the invention (each representative compound is present in a concentration of 4 mcg/ml)

| ESBL Type | Strains | Clavulanic acid | Compound according to Example No. | | | | | | | | | |
|---|---|---|---|---|---|---|---|---|---|---|---|---|
| | | | 20 | 21 | 23 | 1 | 15 | 13 | 14 | 16 | 4 | 17 | 26 |
| Class A ESBL | E. coli W 13353 | 0.25 | 0.25 | 0.25 | 0.5 | 0.25 | 0.25 | 0.25 | 0.25 | 0.25 | 0.25 | 0.25 | 0.25 |
| | E. coli W 13351 | 0.5 | 0.5 | 1 | 1 | 0.5 | 0.5 | 0.5 | 0.5 | 1 | 0.5 | 1 | 1 |
| | E. coli W 13352 | 0.5 | 4 | 2 | 2 | 2 | 2 | 4 | 2 | 4 | 1 | 2 | 4 |
| Class C ESBL | E. coli M 50 | >32 | 2 | 2 | 2 | 1 | 1 | 2 | 1 | 2 | 1 | 1 | 1 |
| | E. coli 7MP | >32 | 8 | 8 | 8 | 4 | 8 | 8 | 4 | 4 | 2 | 4 | 8 |
| | E. coli B 89 | >32 | 4 | 2 | 4 | 2 | 2 | 2 | 2 | 2 | 1 | 2 | 2 |
| KPC ESBL | K. pneumoniae H 520 | >32 | 16 | 8 | 8 | 8 | 2 | 8 | 4 | 4 | 1 | 2 | 4 |
| | K. pneumoniae H 521 | >32 | 16 | 8 | 8 | 8 | 2 | 8 | 4 | 4 | 1 | 2 | 4 |
| | K. pneumoniae H 522 | >32 | 16 | 4 | 8 | 4 | 1 | 4 | 1 | 1 | 1 | 1 | 1 |
| Class D ESBL | A. baumannii 13301 | >32 | >32 | >32 | >32 | >32 | >32 | >32 | >32 | >32 | >32 | >32 | >32 |
| | A. baumannii 13304 | >32 | >32 | >32 | >32 | >32 | 16 | >32 | 32 | >32 | 8 | 16 | 16 |

(f) heterocyclyl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, and $NHCONR_6R_7$, (g) heteroaryl optionally substituted with one or more substituents independently selected from $C_1$-$C_6$ alkyl, $OR_5$, $NR_6R_7$, halogen, CN, $CONR_6R_7$, $SO_2$-alkyl, $SO_2$-aryl, $OSO_2$-alkyl, $OSO_2$-aryl, and $NHCONR_6R_7$, or (h) $OR_8$;

$R_4$ is:
(a) hydrogen, or
(b) $C_1$-$C_6$ alkyl optionally substituted with one or more substituents independently selected from halogen, $OR_5$, CN, $COOR_5$, $CONR_6R_7$, $NR_6R_7$, $NR_5COR_8$, heterocyclyl, heteroaryl, cycloalkyl and aryl;

$R_5$ and $R_8$ are each independently:
(a) hydrogen, or
(b) $C_1$-$C_6$ alkyl optionally substituted with one or more substituents independently selected from halogen, CN, $CONR_6R_7$, $NR_6R_7$, heterocyclyl, heteroaryl, cycloalkyl and aryl;

$R_6$ and $R_7$ are each independently:
(a) hydrogen, or
(b) $C_1$-$C_6$ alkyl optionally substituted with one or more substituents independently selected from halogen, $OR_5$, CN, $COOR_5$, $CONR_5R_8$, $NR_5R_8$, $NR_5COR_8$, heterocyclyl, heteroaryl, cycloalkyl and aryl.

2. The pharmaceutical composition according to claim 1, wherein the compound of Formula (I) is selected from:

trans-sulfuric acid mono-[2-(5-aminomethyl-[1,3,4]-oxadiazol-2-yl)-7-oxo-1,6-diazabicyclo[3.2.1]-octan-6-yl]ester;

trans-sulfuric acid mono-[2-(5-((S)-1-amino-ethyl)-[1,3,4]-oxadiazol-2-yl)-7-oxo-1,6-diazabicyclo[3.2.1]-octan-6-yl]ester;

trans-sulfuric acid mono-[2-(5-((R)-1-amino-ethyl)-[1,3,4]-oxadiazol-2-yl)-7-oxo-1,6-diazabicyclo[3.2.1]-octan-6-yl]ester;

trans-sulfuric acid mono-[2-(5-(piperidin-4-yl)-[1,3,4]-oxadiazol-2-yl)-7-oxo-1,6-diazabicyclo[3.2.1]-octan-6-yl]ester;

trans-sulfuric acid mono-[2-(5-((S)-pyrrolidin-2-yl)-[1,3,4]-oxadiazol-2-yl)-7-oxo-1,6-diazabicyclo[3.2.1]-octan-6-yl]ester;

trans-sulfuric acid mono-[2-(5-(piperazin-1-yl-methyl)-[1,3,4]-oxadiazol-2-yl)-7-oxo-1,6-diazabicyclo[3.2.1]-octan-6-yl]ester;

trans-sulfuric acid mono-[2-(5-((RS)-amino-1-phenyl-methyl)-[1,3,4]-oxadiazol-2-yl)-7-oxo-1,6-diazabicyclo[3.2.1]-octan-6-yl]ester;

trans-sulfuric acid mono-[2-(5-(piperidin-4-yl)-[1,2,4]-oxadiazol-3-yl)-7-oxo-1,6-diazabicyclo[3.2.1]-octane;

trans-sulfuric acid mono-[2-(5-((R)-piperidin-3-yl)-[1,3,4]-oxadiazol-2-yl)-7-oxo-1,6-diazabicyclo[3.2.1]-octane;

and stereoisomers and a pharmaceutically acceptable salts thereof.

3. The pharmaceutical composition according to claim 1, wherein the compound of Formula (I) is selected from:

Sodium salt of trans-6-(sulphooxy)-2-(5-methyl-[1,3,4]-oxadiazol-2-yl)-7-oxo-1,6-diazabicyclo[3.2.1]-octane;

Sodium salt of trans-6-(sulphooxy)-2-(5-ethyl-[1,3,4]-oxadiazol-2-yl)-7-oxo-1,6-diazabicyclo[3.2.1]-octane;

Sodium salt of trans-6-(sulphooxy)-2-(5-trifluoromethyl-[1,3,4]-oxadiazol-2-yl)-7-oxo-1,6-diazabicyclo[3.2.1]-octane;

Sodium salt of trans-6-(sulphooxy)-2-(5-carboxamido-[1,3,4]-oxadiazol-2-yl)-7-oxo-1,6-diazabicyclo[3.2.1]-octane;

Sodium salt of trans-6-(sulphooxy)-2-(5-(isooxazol-3-yl)-[1,3,4]-oxadiazol-2-yl)-7-oxo-1,6-diazabicyclo[3.2.1]-octane;

Sodium salt of trans-6-(sulphooxy)-2-(5-(furan-2-yl)-[1,3,4]-oxadiazol-2-yl)-7-oxo-1,6-diazabicyclo[3.2.1]-octane;

Sodium salt of trans-6-(sulphooxy)-2-(5-phenyl-[1,3,4]-oxadiazol-2-yl)-7-oxo-1,6-diazabicyclo[3.2.1]-octane;

Sodium salt of trans-6-(sulphooxy)-2-(5-(pyridin-2-yl)-[1,3,4]-oxadiazol-2-yl)-7-oxo-1,6-diazabicyclo[3.2.1]-octane;

Sodium salt of trans-6-(sulphooxy)-2-(5-(6-carboxamido-pyridin-2-yl)-[1,3,4]-oxadiazol-2-yl)-7-oxo-1,6-diazabicyclo[3.2.1]-octane;

Sodium salt of trans-6-(sulphooxy)-2-(5-(5,6-dihydro-8H-imidazo[2,1-c][1,4]-oxazin-2-yl)-[1,3,4]-oxadiazol-2-yl)-7-oxo-1,6-diazabicyclo[3.2.1]-octane;

Sodium salt of trans-6-(sulphooxy)-2-(5-(morpholino-4-methyl)-[1,3,4]-oxadiazol-2-yl)-7-oxo-1,6-diazabicyclo[3.2.1]-octane;

Sodium salt of trans-sulfuric acid mono-[2-(5-(morpholin-4-yl-carbonyl)-[1,3,4]-oxadiazol-2-yl)-7-oxo-1,6-diazabicyclo[3.2.1]-octan-6-yl]ester;

Sodium salt of trans-6-(sulphooxy)-2-(5-methy-[1,3,4]-thiadiazol-2-yl)-7-oxo-1,6-diazabicyclo[3.2.1]-octane;

Sodium salt of trans-6-(sulphooxy)-2-(5-methyl-[1,2,4]-oxadiazol-3-yl)-7-oxo-1,6-diazabicyclo[3.2.1]-octane;

Sodium salt of trans-6-(sulphooxy)-2-(5-ethoxycarbonyl-[1,2,4]-oxadiazol-3-yl)-7-oxo-1,6-diazabicyclo[3.2.1]-octane;

Sodium salt of trans-6-(sulphooxy)-2-(2-methyl-2H-[1,2,3,4]-tetrazol-5-yl)-7-oxo-1,6-diazabicyclo[3.2.1]-octane;

Sodium salt of trans-6-(sulphooxy)-2-(1-methyl-1H-[1,2,3,4]-tetrazol-5-yl)-7-oxo-1,6-diazabicyclo[3.2.1]-octane;

Sodium salt of trans-6-(sulphooxy)-2-(3-ethoxycarbonyl-[1,2,4]-oxadiazol-5-yl)-7-oxo-1,6-diazabicyclo[3.2.1]-octane;

Sodium salt of trans-6-(sulphooxy)-2-(5-carboxamido-[1,2,4]-oxadiazol-3-yl)-7-oxo-1,6-diazabicyclo[3.2.1]-octane;

and stereoisomers thereof.

4. A pharmaceutical composition comprising: (a) at least one beta-lactamase inhibitor selected from sulbactam, tazobactam, clavulanic acid, and pharmaceutically acceptable derivatives thereof; and (b) the compound of Formula (I) according to any one of claims 1 to 3.

5. The pharmaceutical composition according to claim 1, further comprising at least one beta-lactamase inhibitor selected from sulbactam, tazobactam, clavulanic acid, and pharmaceutically acceptable derivatives thereof.

6. The pharmaceutical composition according to claim 1, wherein the antibacterial agent is selected from the group consisting of aminoglycosides, ansamycins, carbacephems, cephalosporins, cephamycins, lincosamides, lipopeptides, macrolides, monobactams, nitrofurans, penicillins, polypeptides, quinolones, penems, carbapenems, sulfonamides, tetracyclines, and oxazolidinone antibacterial agents.

7. The pharmaceutical composition according to claim 1, wherein the antibacterial agent is selected from the group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, ceftaroline, ceftolozane, piperacillin, doripenem, meropenem, imipenem and latamoxef.

8. A method for treating bacterial infection in a subject, said method comprising administering to said subject a pharmaceutically effective amount of a pharmaceutical composition according to claim 1.

9. A method for treating a bacterial infection in a subject, said method comprising administering to said subject a pharmaceutically effective amount of: (a) a compound of Formula (I) according to claim 1 or a stereoisomer or a pharmaceutically acceptable salt thereof, and (b) at least one beta-lactamase inhibitor selected from sulbactam, tazobactam, clavulanic acid, and pharmaceutically acceptable derivatives thereof.

10. A method for treating a bacterial infection in a subject, said method comprising administering to said subject a pharmaceutically effective amount of: (a) a compound of Formula (I) according to claim 1 or a stereoisomer or a pharmaceutically acceptable salt thereof, and (b) at least one antibacterial agent or a pharmaceutically acceptable derivative thereof.

11. A method for treating a bacterial infection in a subject, said method comprising administering to said subject a pharmaceutically effective amount of: (a) a compound of Formula (I) according to claim 1 or a stereoisomer or a pharmaceutically acceptable salt thereof; (b) at least one beta-lactamase inhibitor selected from sulbactam, tazobactam, clavulanic acid, and pharmaceutically acceptable derivatives thereof; and (c) at least one antibacterial agent or a pharmaceutically acceptable derivative thereof.

12. A method for increasing antibacterial effectiveness of an antibacterial agent in a subject, said method comprising co-administering said antibacterial agent or a pharmaceutically acceptable derivative thereof with a pharmaceutically effective amount of a compound of Formula (I) according to claim 1, or a stereoisomer or a pharmaceutically acceptable salt thereof.

13. The method according to any one of claims 8, 10, 11 and 12, wherein the antibacterial agent is selected from the group consisting of aminoglycosides, ansamycins, carbacephems, cephalosporins, cephamycins, lincosamides, lipopeptides, macrolides, monobactams, nitrofurans, penicillins, polypeptides, quinolones, penems, carbapenems, sulfonamides, tetracyclines, and oxazolidinone antibacterial agents.

14. The method according to any one of claims 8, 10, 11 and 12, wherein the antibacterial agent is a beta-lactam antibacterial agent.

15. The method according to any one of claims 8, 10, 11 and 12, wherein the antibacterial agent is selected from the group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, ceftaroline, ceftolozane, latamoxef, piperacillin, doripenem, meropenem and imipenem.

16. A method for treating bacterial infection in a subject, said method comprising administering to said subject a pharmaceutically effective amount of a pharmaceutical composition according to claim 4.

17. A method for treating bacterial infection in a subject, said method comprising administering to said subject a pharmaceutically effective amount of a pharmaceutical composition according to claim 5.

18. The pharmaceutical composition according to claim 1 or the method according to any one of claims 8, 10, 11 and 12, wherein the antibacterial agent is a beta-lactam antibacterial agent.

* * * * *